(12) United States Patent
Saidha et al.

(10) Patent No.: US 8,784,452 B2
(45) Date of Patent: *Jul. 22, 2014

(54) TRANSCONNECTOR

(75) Inventors: Sean Saidha, Basel (CH); William L. Strausbaugh, Newmanstown, PA (US); Boyd Wolf, Coatesville, PA (US); Thomas Pepe, Turnersville, NJ (US); Christoph Roth, Muttenz (CH); David S. Rathbun, Gap, PA (US); William P. McDonough, Collegeville, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 127 days.

This patent is subject to a terminal disclaimer.

(21) Appl. No.: 13/598,920

(22) Filed: Aug. 30, 2012

(65) Prior Publication Data

US 2013/0006306 A1    Jan. 3, 2013

Related U.S. Application Data

(63) Continuation of application No. 12/442,647, filed as application No. PCT/US2007/079426 on Sep. 25, 2007, now Pat. No. 8,277,489.

(60) Provisional application No. 60/827,016, filed on Sep. 26, 2006.

(51) Int. Cl.
*A61B 17/70* (2006.01)

(52) U.S. Cl.
CPC .................................. *A61B 17/7049* (2013.01)
USPC ........................................... 606/250; 606/251

(58) Field of Classification Search
CPC ........................... A61B 17/7049; A61B 17/705
USPC ........... 606/246–279; 411/386, 411–413, 423
See application file for complete search history.

(56) References Cited

U.S. PATENT DOCUMENTS

| 2,330,095 | A | 11/1941 | Venditty |
| 4,257,409 | A | 3/1981 | Bacal et al. |

(Continued)

FOREIGN PATENT DOCUMENTS

| DE | 3219575 | 12/1983 |
| DE | 3639810 A1 | 5/1988 |

(Continued)

OTHER PUBLICATIONS

Synthes Spine Sale Brochure: Cervifix System, dated 2001.
Notification of Transmittal of the International Search Report, dated Aug. 7, 2008, in International Application No. PCT/US07/79426.
Notification of Transmittal of the International Preliminary Report on Patentability, dated Dec. 19, 2008, in International Application No. PCT/US07/79426.

(Continued)

*Primary Examiner* — Ellen C Hammond
*Assistant Examiner* — Stuart S Bray
(74) *Attorney, Agent, or Firm* — Meunier Carlin & Curfman, LLC

(57) ABSTRACT

A transconnector for joining adjacent longitudinal spinal rods. The transconnector preferably includes a bridge member and a pair of bone fixation coupling elements, the bridge member is preferably sized and configured to span a distance between the pair of bone fixation coupling elements. The bone fixation coupling elements are preferably sized and configured to engage the bridge member and sized and configured to receive one of the bone fixation elements. The bone fixation coupling elements are preferably sized and configured to engage the body portion of the bone fixation element. The bone fixation coupling elements may include a locking cap having a first set of threads for threadably engaging the bone fixation element.

19 Claims, 18 Drawing Sheets

(56) References Cited

U.S. PATENT DOCUMENTS

| | | | |
|---|---|---|---|
| 4,258,607 A * | 3/1981 | McKewan | 411/417 |
| 4,369,770 A | 1/1983 | Bacal et al. | |
| 4,433,677 A | 2/1984 | Ulrich et al. | |
| 4,611,582 A | 9/1986 | Duff | |
| 4,815,453 A | 3/1989 | Cotrel | |
| 4,955,885 A | 9/1990 | Meyers | |
| 4,981,406 A * | 1/1991 | Weiss et al. | 411/386 |
| 4,998,936 A | 3/1991 | Mehdian | |
| 5,005,562 A | 4/1991 | Cotrel | |
| 5,010,879 A | 4/1991 | Moriya et al. | |
| 5,084,049 A | 1/1992 | Asher et al. | |
| 5,147,360 A | 9/1992 | Dubousset | |
| 5,154,718 A | 10/1992 | Cozad et al. | |
| 5,209,752 A | 5/1993 | Ashman et al. | |
| 5,261,907 A | 11/1993 | Vignaud et al. | |
| 5,261,913 A | 11/1993 | Marnay | |
| 5,275,600 A | 1/1994 | Allard et al. | |
| 5,312,405 A | 5/1994 | Korotko et al. | |
| 5,334,203 A | 8/1994 | Wagner | |
| 5,366,455 A | 11/1994 | Dove et al. | |
| 5,423,818 A | 6/1995 | Van Hoeck et al. | |
| 5,437,671 A | 8/1995 | Lozier et al. | |
| 5,439,463 A | 8/1995 | Lin | |
| 5,476,462 A | 12/1995 | Allard et al. | |
| 5,498,263 A | 3/1996 | DiNello et al. | |
| 5,507,746 A | 4/1996 | Lin | |
| 5,522,816 A | 6/1996 | DiNello et al. | |
| 5,527,314 A | 6/1996 | Brumfield et al. | |
| 5,531,747 A | 7/1996 | Ray | |
| 5,534,002 A | 7/1996 | Brumfield et al. | |
| 5,549,607 A | 8/1996 | Olson et al. | |
| 5,569,246 A | 10/1996 | Ojima et al. | |
| 5,575,791 A | 11/1996 | Lin | |
| 5,601,552 A | 2/1997 | Cotrel | |
| 5,620,444 A | 4/1997 | Assaker | |
| 5,624,442 A | 4/1997 | Mellinger et al. | |
| 5,630,816 A | 5/1997 | Kambin | |
| 5,651,789 A | 7/1997 | Cotrel | |
| 5,667,506 A | 9/1997 | Sutterlin | |
| 5,667,507 A | 9/1997 | Corin et al. | |
| 5,669,910 A | 9/1997 | Korhonen et al. | |
| 5,676,665 A | 10/1997 | Bryan | |
| 5,681,312 A | 10/1997 | Yuan et al. | |
| 5,688,272 A | 11/1997 | Montague et al. | |
| 5,693,053 A | 12/1997 | Estes | |
| 5,702,392 A | 12/1997 | Wu et al. | |
| 5,707,372 A | 1/1998 | Errico et al. | |
| 5,709,684 A | 1/1998 | Errico et al. | |
| 5,716,355 A | 2/1998 | Jackson et al. | |
| 5,752,955 A | 5/1998 | Errico | |
| 5,863,167 A * | 1/1999 | Kaneko | 411/426 |
| 5,885,284 A | 3/1999 | Errico | |
| 5,899,903 A | 5/1999 | Cotrel | |
| 5,947,966 A | 9/1999 | Dewry | |
| 5,980,523 A | 11/1999 | Jackson | |
| 5,984,923 A | 11/1999 | Breard | |
| 5,989,251 A | 11/1999 | Nichols | |
| 6,096,039 A | 8/2000 | Stoltenberg et al. | |
| 6,110,173 A | 8/2000 | Thomas, Jr. | |
| 6,113,600 A | 9/2000 | Drummond et al. | |
| 6,136,000 A | 10/2000 | Louis et al. | |
| 6,136,003 A | 10/2000 | Hoeck et al. | |
| 6,171,311 B1 | 1/2001 | Richelsoph | |
| 6,217,578 B1 | 4/2001 | Crozet et al. | |
| 6,234,705 B1 | 5/2001 | Troxell | |
| 6,238,396 B1 | 5/2001 | Lombardo | |
| 6,261,288 B1 | 7/2001 | Jackson | |
| 6,264,658 B1 | 7/2001 | Lee et al. | |
| 6,283,967 B1 | 9/2001 | Troxell et al. | |
| 6,302,882 B1 | 10/2001 | Lin et al. | |
| 6,306,137 B2 | 10/2001 | Troxell | |
| 6,328,741 B1 | 12/2001 | Richelsoph | |
| 6,355,038 B1 | 3/2002 | Pisharodi | |
| 6,402,751 B1 | 6/2002 | Hoeck et al. | |
| 6,413,258 B1 | 7/2002 | Bernhardt, Jr. | |
| 6,432,108 B1 | 8/2002 | Burgess et al. | |
| 6,524,310 B1 | 2/2003 | Lombardo et al. | |
| 6,551,318 B1 | 4/2003 | Stahurski | |
| 6,554,832 B2 | 4/2003 | Shluzas | |
| 6,562,040 B1 | 5/2003 | Wagner | |
| 6,589,243 B1 | 7/2003 | Viart et al. | |
| 6,602,253 B2 | 8/2003 | Richelsoph et al. | |
| 6,602,254 B2 | 8/2003 | Gertzein et al. | |
| 6,616,668 B2 | 9/2003 | Altarac et al. | |
| 6,685,411 B2 * | 2/2004 | Kato | 411/386 |
| 6,736,817 B2 | 5/2004 | Troxell et al. | |
| 6,796,761 B2 * | 9/2004 | Mizuno et al. | 411/386 |
| 6,887,241 B1 | 5/2005 | McBride et al. | |
| 6,904,835 B2 * | 6/2005 | Dugan et al. | 81/446 |
| 6,918,727 B2 * | 7/2005 | Huang | 411/389 |
| 7,137,986 B2 | 11/2006 | Troxell et al. | |
| 7,213,999 B2 * | 5/2007 | Haas | 403/337 |
| 7,481,827 B2 | 1/2009 | Ryan et al. | |
| 7,645,294 B2 * | 1/2010 | Kalfas et al. | 606/250 |
| 7,866,930 B2 * | 1/2011 | Murase et al. | 411/386 |
| 7,867,255 B2 * | 1/2011 | Miller et al. | 606/250 |
| 7,892,260 B2 * | 2/2011 | Mahoney et al. | 606/265 |
| 7,967,845 B2 * | 6/2011 | Lauryssen et al. | 606/250 |
| 8,012,188 B2 * | 9/2011 | Melkent et al. | 606/286 |
| 8,034,082 B2 * | 10/2011 | Lee et al. | 606/250 |
| 8,137,386 B2 * | 3/2012 | Jackson | 606/266 |
| 8,192,471 B2 * | 6/2012 | Ludwig et al. | 606/265 |
| 8,197,170 B2 * | 6/2012 | Wagner | 411/386 |
| 8,211,109 B2 * | 7/2012 | Groiso | 606/75 |
| 8,221,466 B2 * | 7/2012 | Asaad et al. | 606/252 |
| 8,226,652 B2 * | 7/2012 | Michelson | 606/60 |
| 8,246,657 B1 * | 8/2012 | Samuel | 606/250 |
| 8,439,617 B2 * | 5/2013 | Strom | 411/386 |
| 2002/0052603 A1 | 5/2002 | Nichols et al. | |
| 2002/0082599 A1 | 6/2002 | Crandall et al. | |
| 2002/0138077 A1 | 9/2002 | Ferree | |
| 2002/0143327 A1 | 10/2002 | Shluzas | |
| 2002/0143330 A1 | 10/2002 | Shluzas | |
| 2002/0169448 A1 | 11/2002 | Vanacker | |
| 2002/0169450 A1 | 11/2002 | Lange | |
| 2002/0169451 A1 | 11/2002 | Yeh | |
| 2003/0004512 A1 | 1/2003 | Farris et al. | |
| 2003/0028192 A1 | 2/2003 | Schar et al. | |
| 2003/0045874 A1 | 3/2003 | Thomas, Jr. | |
| 2003/0050640 A1 | 3/2003 | Lee et al. | |
| 2003/0059275 A1 * | 3/2003 | Mizuno et al. | 411/386 |
| 2003/0083659 A1 | 5/2003 | Lin et al. | |
| 2004/0092931 A1 | 5/2004 | Taylor et al. | |
| 2005/0192572 A1 | 9/2005 | Abdelgany et al. | |
| 2005/0228326 A1 | 10/2005 | Kalfas et al. | |
| 2005/0228377 A1 * | 10/2005 | Chao et al. | 606/61 |
| 2005/0265806 A1 * | 12/2005 | Craven | 411/386 |
| 2006/0009766 A1 * | 1/2006 | Lee et al. | 606/61 |
| 2006/0064091 A1 | 3/2006 | Ludwig et al. | |
| 2006/0206114 A1 | 9/2006 | Ensign et al. | |
| 2007/0160440 A1 * | 7/2007 | Langewiesche | 411/386 |
| 2007/0217887 A1 * | 9/2007 | Lin | 411/413 |
| 2009/0060676 A1 * | 3/2009 | Murase et al. | 411/386 |
| 2010/0084449 A1 * | 4/2010 | Columbia | 224/520 |
| 2010/0152786 A1 * | 6/2010 | Behrbalk | 606/301 |
| 2012/0056423 A1 * | 3/2012 | Jung | 285/390 |
| 2012/0248768 A1 * | 10/2012 | Fischer | 285/405 |

FOREIGN PATENT DOCUMENTS

| | | |
|---|---|---|
| DE | 4330837 A1 | 9/1993 |
| EP | 0811357 A1 | 12/1997 |
| EP | 0813845 A1 | 12/1997 |
| EP | 0953316 A1 | 11/1999 |
| EP | 1295566 A1 | 3/2003 |
| FR | 2615095 A1 | 11/1988 |
| FR | 2645427 | 4/1989 |
| FR | 2714590 | 1/1994 |
| JP | 2002355252 | 12/2002 |
| WO | 0057801 A1 | 10/2000 |
| WO | 0238061 | 5/2002 |

(56) References Cited

FOREIGN PATENT DOCUMENTS

| WO | 2005096974 | 10/2005 |
| WO | 2008039777 A2 | 4/2008 |

OTHER PUBLICATIONS

Official U.S. Office Action, dated Jan. 27, 2012, in related U.S. Appl. No. 12/442,647.

* cited by examiner

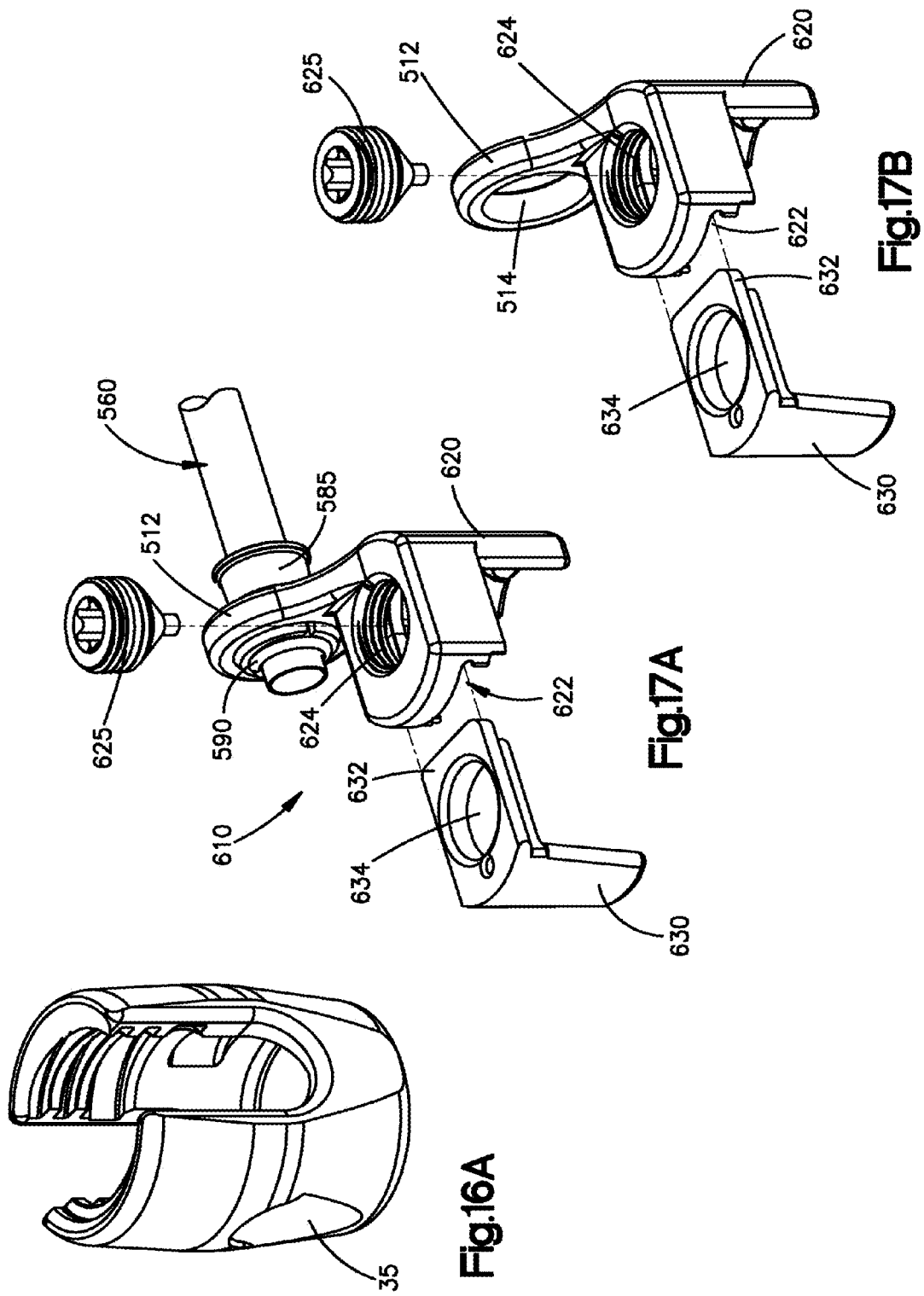

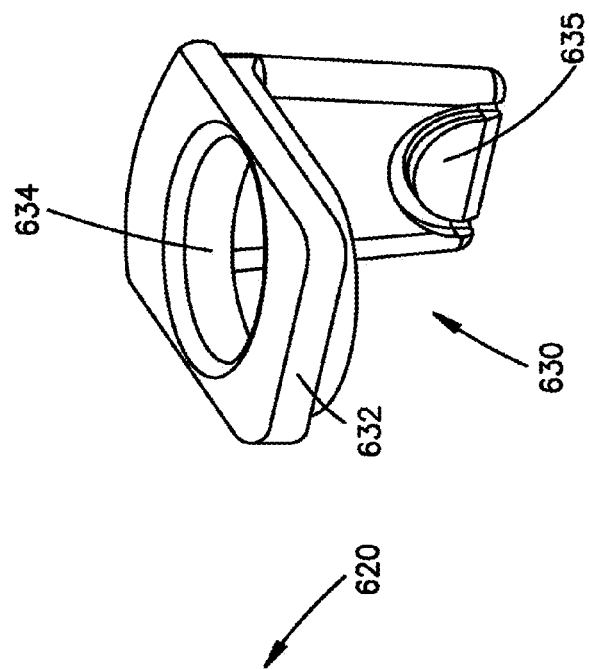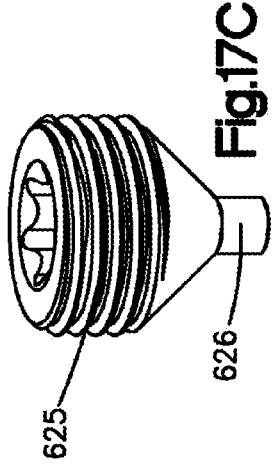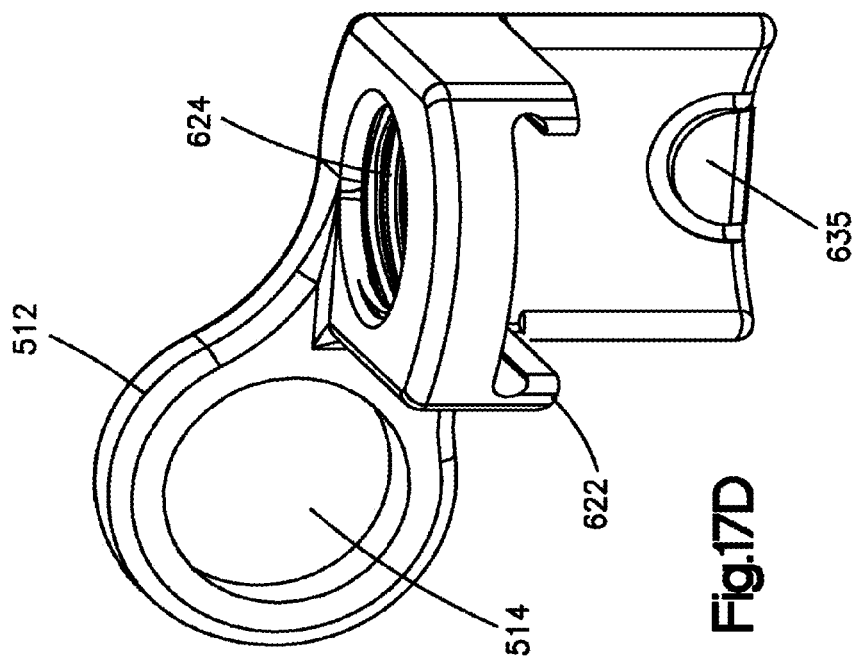

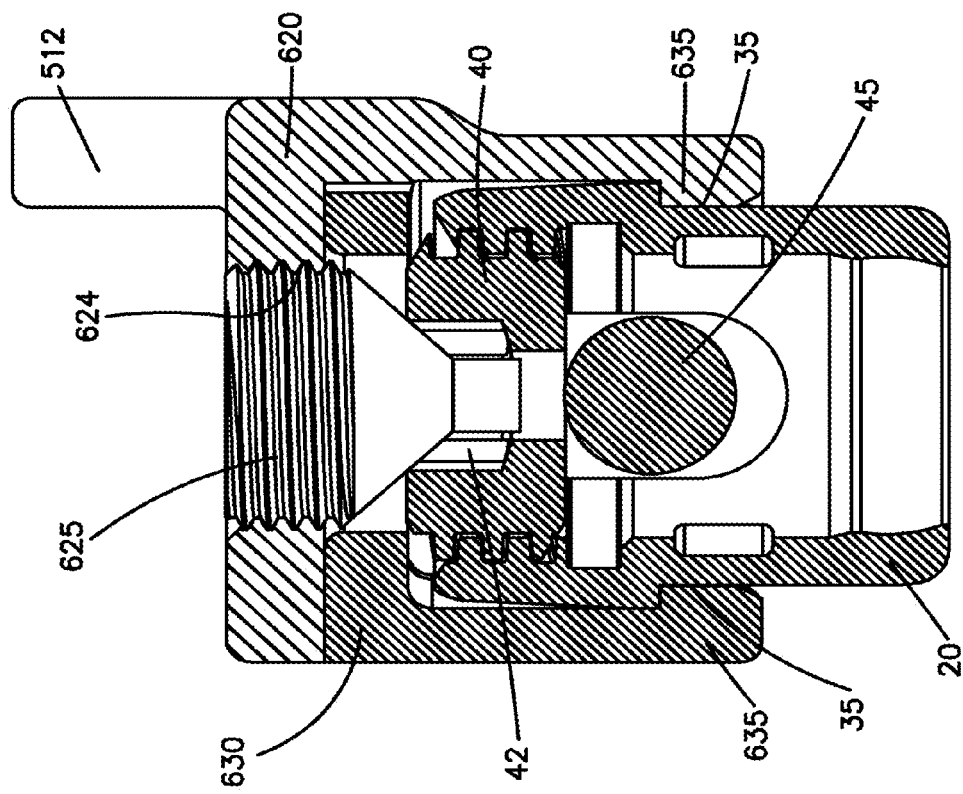
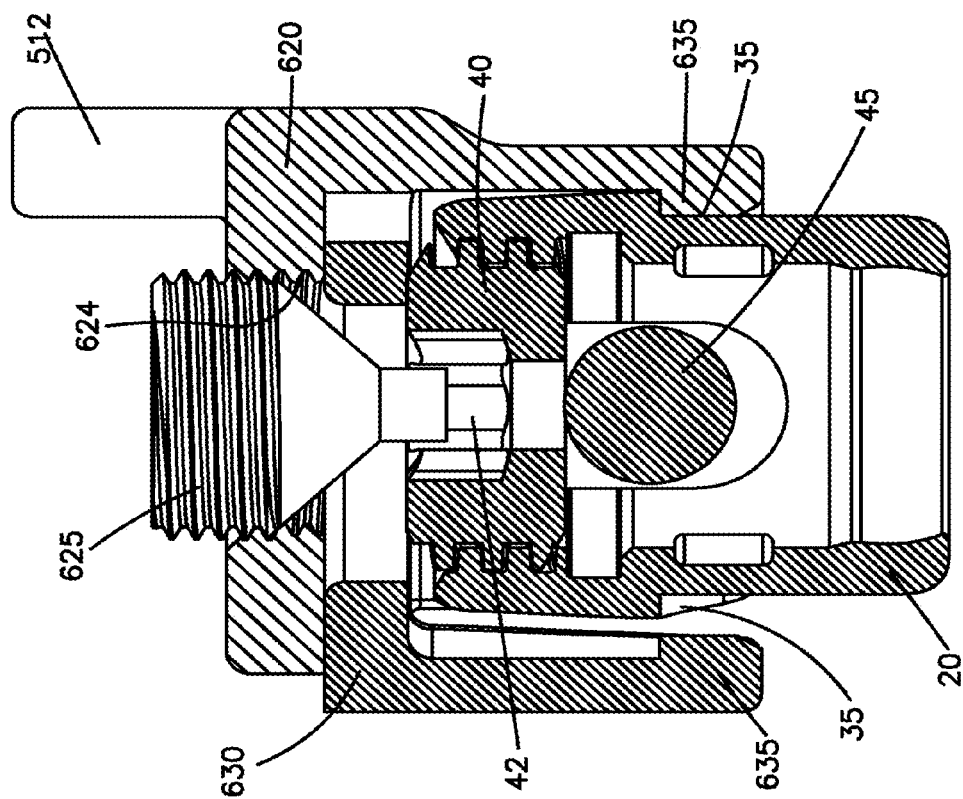

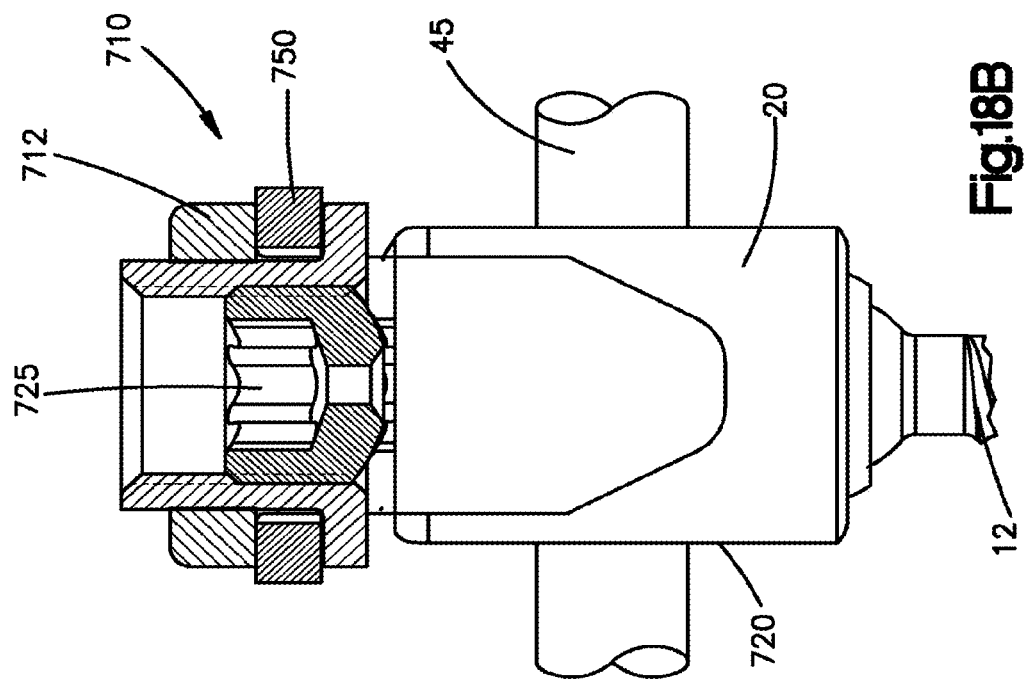
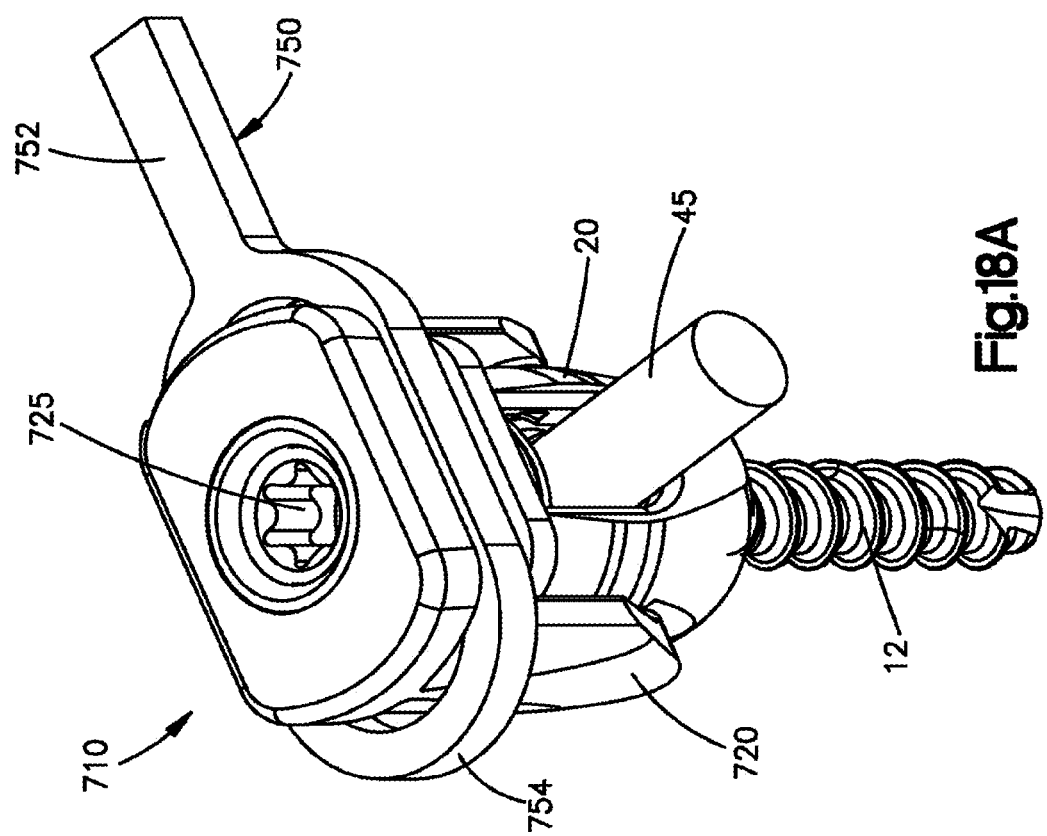
Fig.18B
Fig.18A

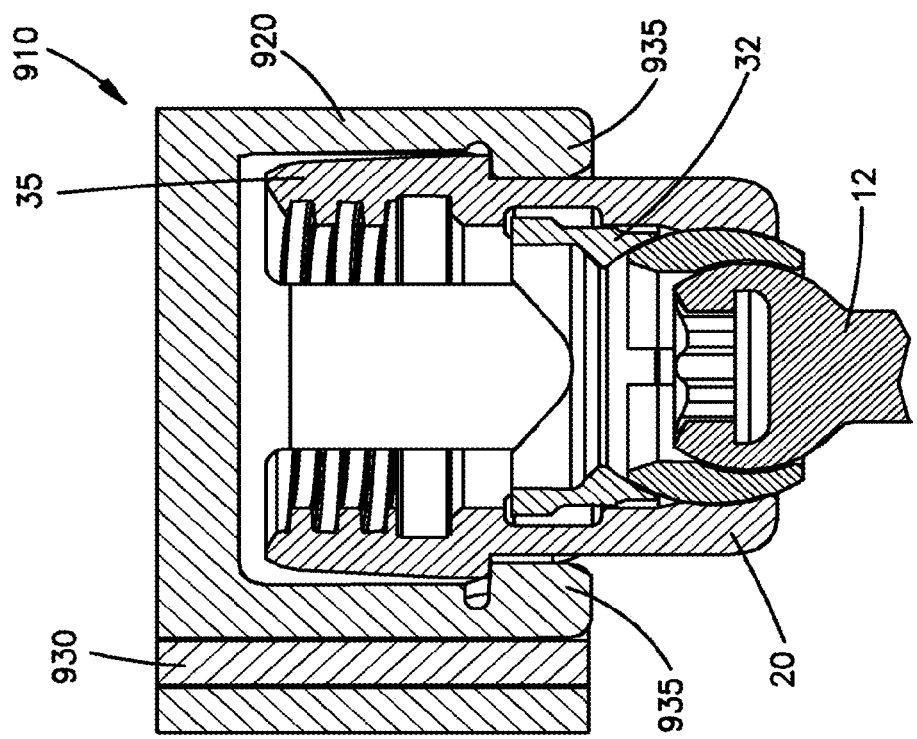
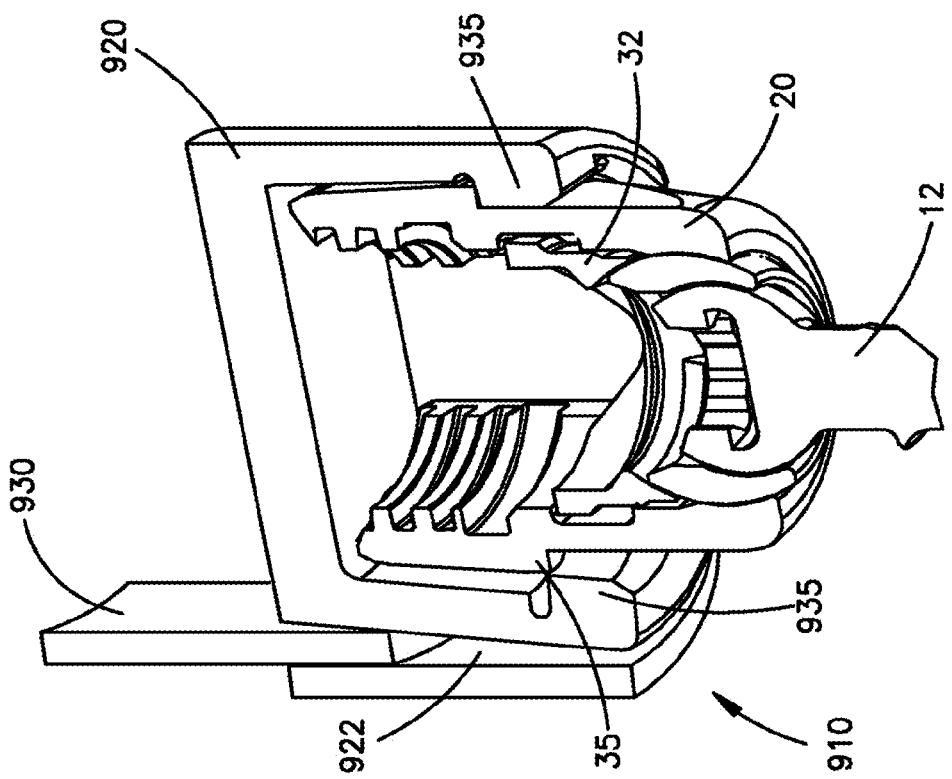
Fig.20B
Fig.20A

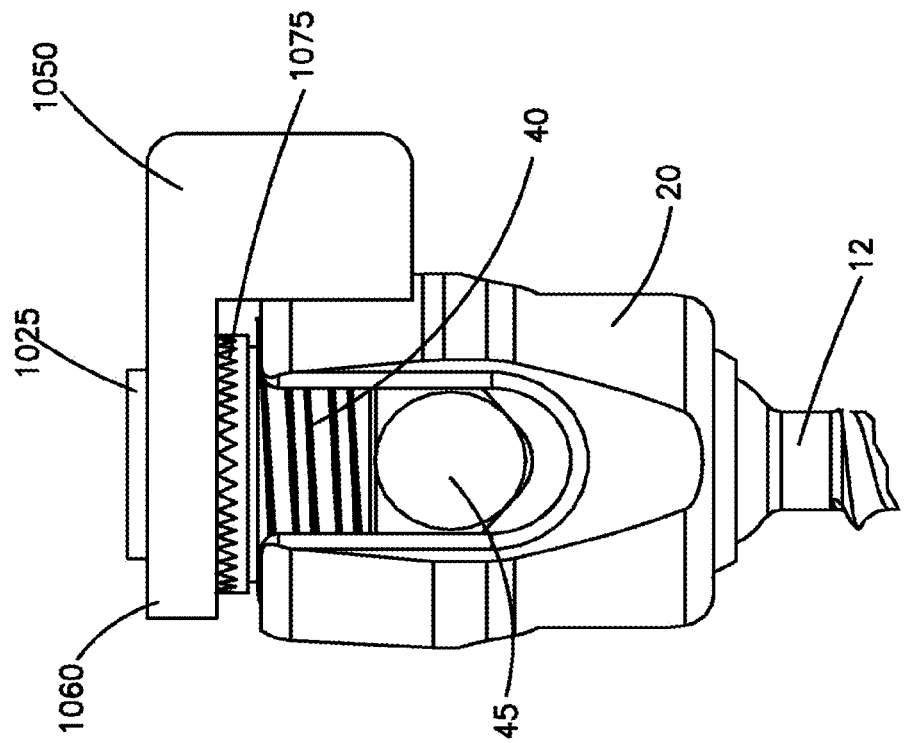
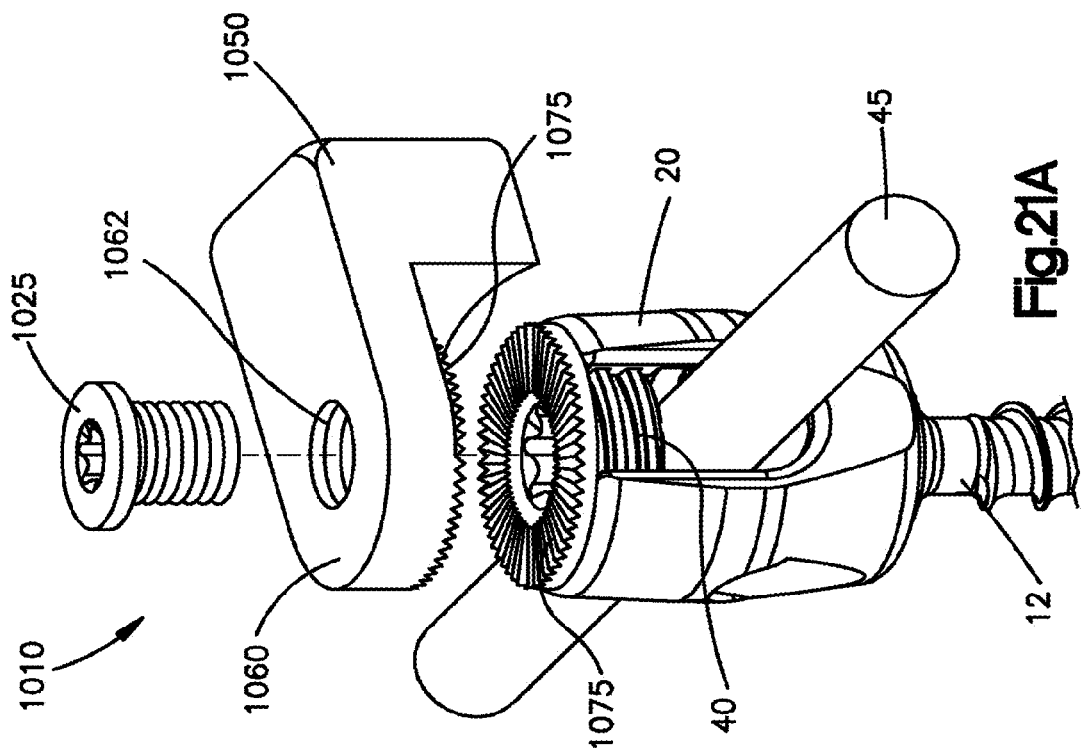

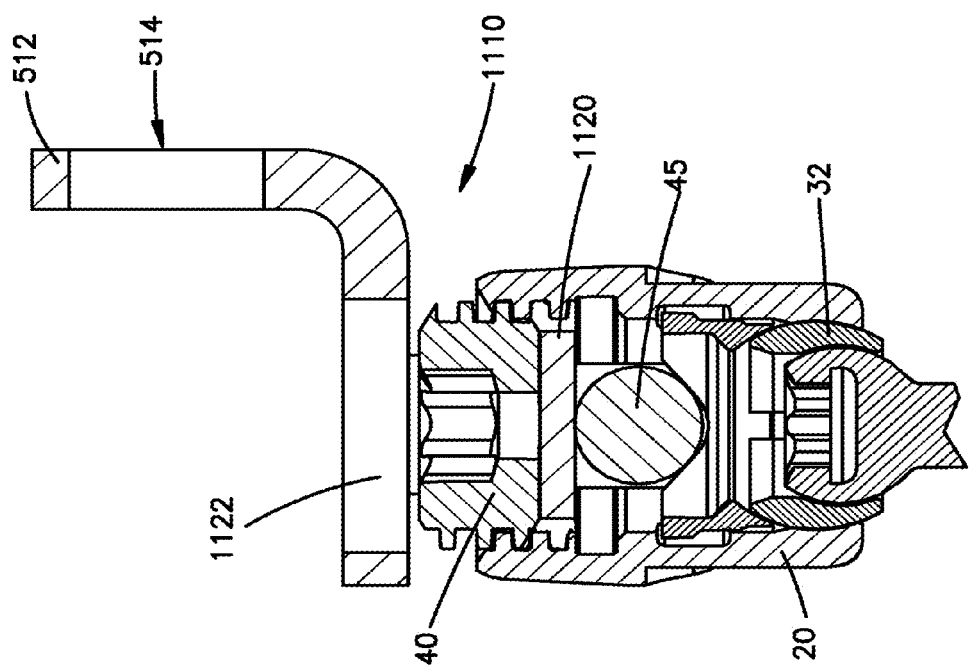
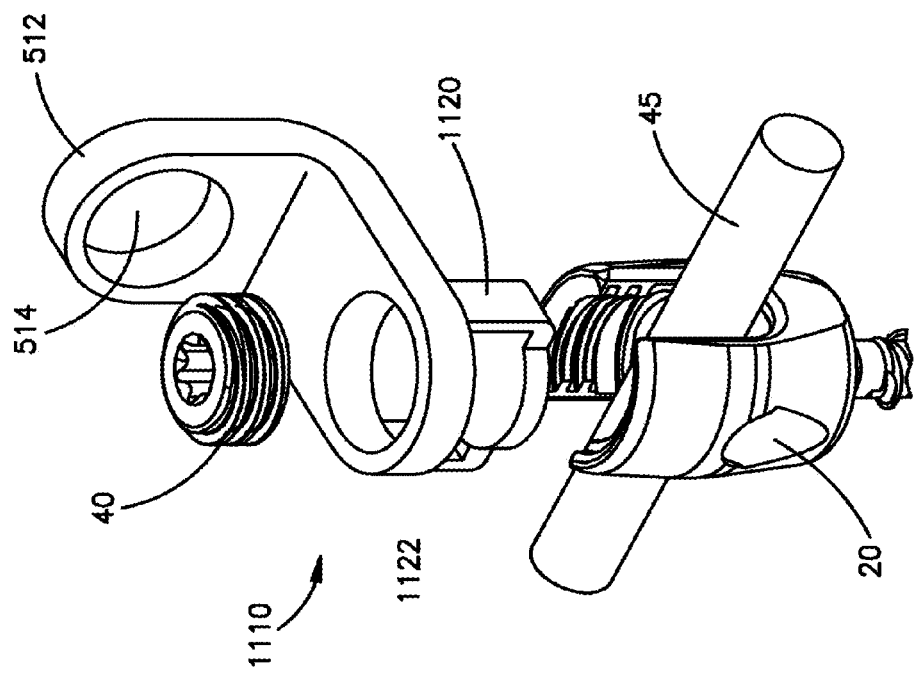
Fig.22A
Fig.22B

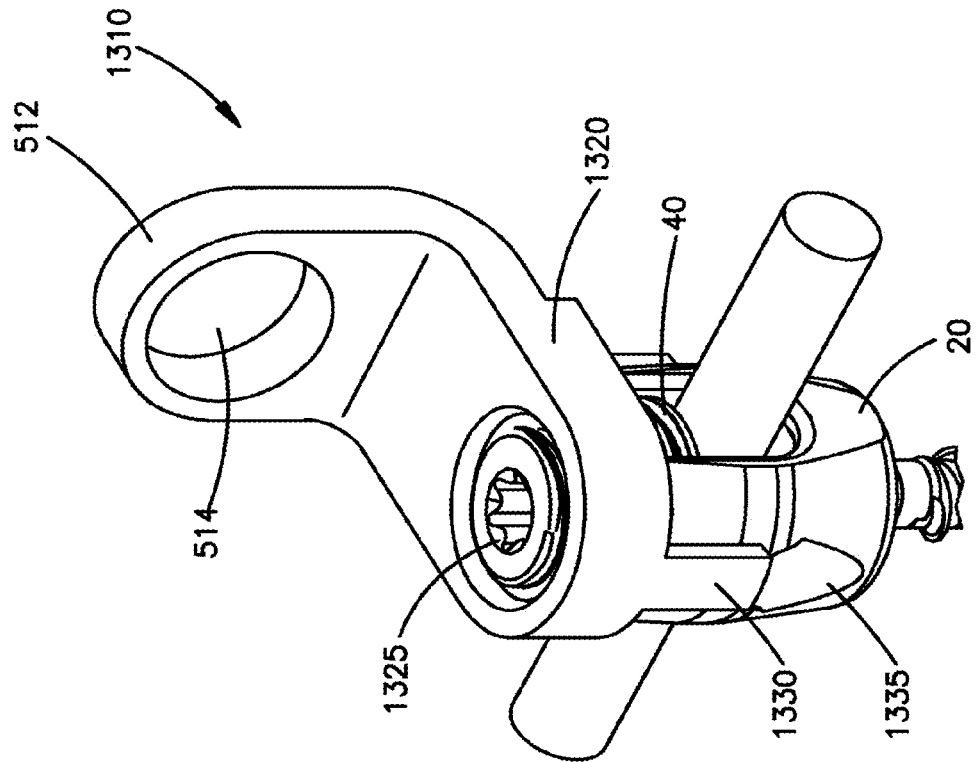
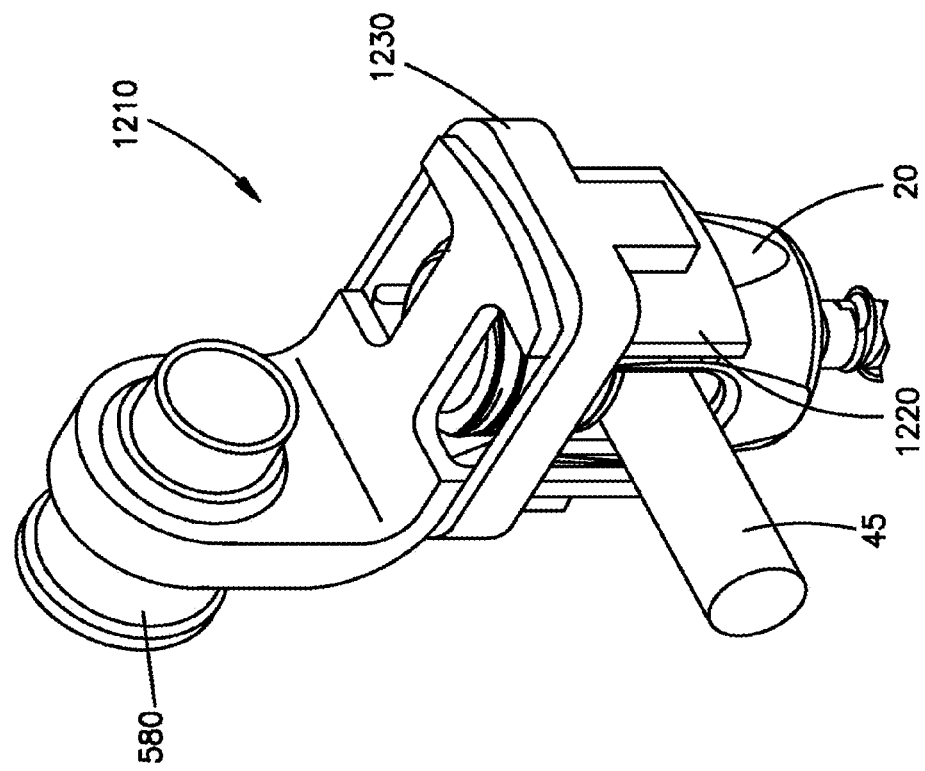
Fig.24
Fig.23

TRANSCONNECTOR

CROSS REFERENCE TO RELATED APPLICATIONS

This application is a continuation of U.S. patent application Ser. No. 12/442,647, filed Dec. 23, 2009 and entitled "Transconnector." This application also claims priority to PCT/US2007/079426, filed Sep. 25, 2007, and U.S. Provisional Patent Application No. 60/827,016, filed Sep. 26, 2006. The contents of the above-referenced applications are hereby incorporated by reference in their entireties.

FIELD OF THE INVENTION

The present invention relates to a device for spinal fixation, and in particular to a transconnector for coupling longitudinal spinal rods, or other elongated members.

BACKGROUND OF THE INVENTION

Spinal fusion is a procedure that involves joining two or more adjacent vertebrae with a spinal fixation device to restrict movement of the vertebra with respect to one another. For a number of known reasons, spinal fixation devices are used in spine surgery to align and/or fix a desired relationship between adjacent vertebral bodies. Such devices typically include a pair of spinal fixation elements, such as, for example, a relatively rigid fixation rod, a dynamic or flexible spinal rod, a plate, etc., longitudinally placed on the posterior spine on either side of spinous processes of the vertebral column. The spinal fixation elements being coupled to adjacent vertebrae by attaching the spinal fixation element to various bone fixation elements, such as, for example, hooks, bolts, wires, screws, etc. The bone fixation elements commonly include body portions with rod-receiving channels in which the spinal fixation element is inserted and subsequently clamped. Surgeons may commonly choose to install multiple bone fixation elements, as well as multiple spinal fixation elements, to treat a given spinal disorder.

The spinal fixation elements may have a predetermined contour, and once installed, the spinal fixation element may hold the vertebrae in a desired spatial relationship, either until desired healing or spinal fusion has taken place, or for some longer period of time.

It is also well known that the strength and stability of dual spinal rod assemblies can be increased by coupling the two spinal rods with a cross-brace or transconnector which typically extends substantially transverse to the spinal rods and typically substantially horizontally across the spine to interconnect the longitudinal spinal rods. The use of transconnectors, however, can provide surgeons with one or more difficulties. The simplest situation in which a transconnector could be used occurs when the two spinal rods are substantially parallel to each other, i.e. there is no rod convergence or divergence in the medial-lateral direction; where the two spinal rods have the same orientation with respect to the coronal plane viewed in the anterior-posterior direction, i.e. the spinal rods are coplanar from a lateral view; and where the two spinal rods are located at a fixed, predetermined distance from each other. However, due to a wide variety of factors, the two spinal rods are rarely so geometrically aligned in clinical situations.

Thus, it is advantageous to provide a transconnector which may be adjusted to adapt to variations in spinal rod alignment. The addition of such adjustability, however, may require the transconnector to include numerous pieces that can be difficult to assemble and use while in the surgical environment.

Furthermore, when transconnectors are placed over adjacent spinal rods, the extended profile of the device may often result in soft tissue trauma. Thus, it is advantageous to provide a transconnector with as small a lateral (i.e., transverse) profile as possible to decrease the total amount of soft tissue trauma incurred, and to minimize the chance for subsequent complications. Providing a transconnector with a small lateral profile is also beneficial when attempting to engage longitudinal spinal rods wherein, for one reason or another, the bone fixation elements are closely spaced together.

It is further advantageous to provide a transconnector that, once assembled, prevents disassembly of the individual pieces of the transconnector assembly, thereby helping to facilitate installation of the transconnector by reducing the likelihood that the transconnector will accidentally come apart during installation in the patient. It is also advantageous to provide a transconnector that reduces the overall number of steps required to fix the location of the transconnector with respect to the longitudinal spinal rods, thereby facilitating installation of the transconnector by reducing the time and effort needed for installation in the patient.

Thus, there exists a need for an improved transconnector for coupling adjacent spinal rods which advantageously may be adapted to adjust to varying spinal rod alignments, which has a reduced lateral footprint for reducing associated tissue trauma and which when pre-assembled will remain intact during installation in the patient.

SUMMARY OF THE INVENTION

The present invention is directed to a transconnector for joining adjacent longitudinal spinal rods, the spinal rods being secured to a patient's vertebra via a plurality of bone fixation elements. The bone fixation element preferably including a bone anchor and a body portion, the body portion may include a rod-receiving channel and an optional closure cap for securing the spinal rod in the rod-receiving channel.

The transconnector may include a bridge member and first and second bone fixation coupling elements. The bridge member may include first and second ends. The first and second bone fixation coupling elements are preferably sized and configured to: (i) engage the first and second ends of the bridge member and (ii) engage one of the bone fixation elements.

The bone fixation coupling elements are preferably sized and configured to engage the body portion of the bone fixation elements. In one exemplary embodiment, the bone fixation coupling elements may include a fastener, the fastener being sized and configured to engage the bone fixation element. For example, the fastener may be sized and configured to threadably engage a plurality of threads formed on the body portion of the bone fixation element. Alternatively, the fastener may be sized and configured to threadably engage an internal threaded bore formed in the optional closure cap of the bone fixation element.

In another exemplary embodiment, the bone fixation coupling elements may include either a protrusion or recess formed thereon for engaging either a protrusion or recess formed on an outer surface of the body portion of the bone fixation element. Alternatively, the bone fixation coupling elements may engage the body portion of the bone fixation elements via, for example, an interference fit, a press-fit, a snap-fit, or a tongue and groove type connection.

In one exemplary embodiment, the bone fixation coupling elements may each include a locking cap, a bushing and a nut, the bushing being sized and configured to interconnect the locking cap with the bridge member. The locking cap may further include a first set of threads for engaging the bone fixation element, a second set of threads for engaging the nut, and a tapered central portion located in-between the first and second set of threads. The bushing may include an outer surface and a central passage, the central passage being sized and configured to receive the tapered central portion of the locking cap therein. The bone fixation coupling element is moveable between a first position and a second position, wherein when the bone fixation coupling element is in the first position, the bridge member is able to angulate with respect to the locking cap via the bushing and wherein when the bone fixation coupling element is in the second position, the bridge member is fixedly secured with respect to the locking cap. Preferably, rotation of the nut causes the bone fixation coupling element to move from the first position to the second position.

In use, the locking cap may be sized and configured to prevent the bridge member from contacting the bone fixation element. For example, the locking cap may be at least partially tapered, the tapered portion being sized and configured to prevent the bridge member from contacting the bone fixation element. Alternatively, for example, the locking cap may include a ledge for preventing the bridge member from contacting the bone fixation element.

The bridge member may further include at least one hole formed on either end thereof for receiving the locking cap and bushing. At least one of the holes may be in the form of an elongated slot.

The bridge member may be configured as an adjustable length bridge member. That is, the bridge member may include a second member moveably associated with a first member.

In one exemplary embodiment of the bridge member, the first member may be in the form of an outer telescopic rod and the second member may be in the form of an inner telescopic rod, the outer telescopic rod having an internal bore for receiving the inner telescopic rod. The bridge member may further include a ring disposed about the outer telescopic rod, the ring being slidably disposed about the outer telescopic rod from a first position to a second position wherein when the ring is in the first position, the inner telescopic rod is free to move with respect to the outer telescopic rod and wherein when the ring is in the second position the position of the inner telescopic rod is fixed with respect to the outer telescopic rod. The outer telescopic rod may include a plurality of slots extending from an end thereof such that movement of the ring from the first position to the second position compresses at least a portion of the outer telescopic rod against the inner telescopic rod.

In an another exemplary embodiment of the bridge member, the first member may be in the form of a first plate member and the second member may be in the form of a second plate member, the second plate member being slidable relative to the first plate member, and preferably within the first plate member. The first and second plate members may be sized and configured to receive a threaded fastener and an optional nut. The threaded fastener may be sized and configured to extend through a hole formed in the first and second plate members such that rotation of the nut causes the position of the second plate member to be fixed with respect to the position of the first plate member.

In another exemplary embodiment of the bridge member, the first and second members may be pivotally coupled to one another about a pivot axis substantially transverse to a longitudinal axis of the transconnector. In this embodiment, preferably one of the first and second members includes a hole formed therein, the hole being sized and configured to receive a plurality of tabs extending from the other of the first and second members. The bridge member may further include a threaded fastener, the fastener being engageable with one of the first and second members such that rotation of the fastener causes the plurality of tabs to expand thereby causing the position of the first member to be fixed with respect to the second member.

In another exemplary embodiment of the bridge member, the bridge member may be in the form of a lateral rod having a locking element on either end thereof. The locking element being moveable from a first position to a second position, wherein in the first position the locking element permits movement of the lateral rod with respect to the associated bone fixation coupling element and wherein in the second position the locking element fixes the position of the lateral rod with respect to the associated bone fixation coupling element. The locking element may include a locking sleeve and a collar, the collar having a through bore for receiving the locking sleeve so that the collar is slidably positionable along a length of the locking sleeve, the locking sleeve having a through bore for slidably receiving the lateral rod so that the locking sleeve is slidably positionable along the length of the lateral rod. Movement of the collar with respect to the locking sleeve preferably causes the locking element to move from the first position to the second position.

In another exemplary embodiment, the bone fixation coupling element may be sized and configured to receive the body portion of the bone fixation element so that, after the bone fixation element has been installed into the patient's body and the longitudinal spinal rod has been placed within the rod-receiving channel of the bone fixation element, the bone fixation coupling elements can be placed over and pressed down onto the body portion of the bone fixation element. The bone fixation coupling element may be sized and configured to receive the body portion of the bone fixation element via one of an interference fit, a press-fit, a snap-fit, or a tongue and groove type connection. The bone fixation coupling element may further include a locking component, the locking component being slidably moveable with respect to the bone fixation coupling element from a first position to a second position, wherein in the second position the locking component further compresses the bone fixation coupling element into engagement with the body portion of the bone fixation element. Alternatively, the bone fixation coupling element may further include a set screw for threadably engaging at least a portion of the bone fixation element.

In one exemplary embodiment of the bone fixation coupling element, the bone fixation coupling elements may include a housing and a slider, wherein the slider is sized and configured to be slidably received by the housing. Preferably, the slider and housing are slidably connected to one another via a dovetail joint type connection. The bone fixation coupling element may further include a set screw for threadably engaging a threaded hole formed in the housing, rotation of the set screw causing the slider to move with respect to the housing resulting in the slider engaging the bone fixation element.

In another exemplary embodiment of the bone fixation coupling element, the bone fixation coupling elements may include one or more beam elements, the beam elements being sized and configured so that, upon rotation of a set screw, the set screw causes the beam elements to contact the body portion of the bone fixation element to thereby fix the position of the bone fixation coupling element with respect to the bone fixation element.

In another exemplary embodiment of the bone fixation coupling element, the bone fixation coupling elements may include one or more slide elements, wherein slideable movement of the slide elements into a recess formed in the bone fixation coupling elements causes the position of the bone fixation coupling element to be fixed with respect to the bone fixation element.

In another exemplary embodiment of the bone fixation coupling element, the bone fixation coupling elements may include an intermediary component, the intermediary component being sized and configured for insertion into the rod-receiving channel of the bone fixation element for contacting the spinal rod and wherein the intermediary component includes a bore formed therein for receiving a closure cap so that the closure cap can engage the threads formed on the bone fixation element.

In another exemplary embodiment of the bridge member, the bridge member may include a pair of eyelets, one on either end thereof for engaging a recess formed in an outer surface of the bone fixation coupling elements.

In another exemplary embodiment of the bridge member, the bridge member may include an integral bone fixation coupling element, the integral bone fixation coupling element including a threaded bore for threadably receiving a set screw, the set screw being threadably engageable with a closure cap secured to the bone fixation element.

In yet another exemplary embodiment of the transconnector, the transconnector may include a bridge member having a first end and a second end and first and second bone fixation coupling elements. The first and second ends of the bridge member may each include at least one hole for receiving the first and second bone fixation coupling elements, respectively. Each of the bone fixation coupling elements may include a locking cap, a bushing and a nut. The locking cap may include a first set of threads for engaging the bone fixation element, a second set of threads for engaging the nut and a tapered central portion located in-between the first and central set of threads. The bushing may include an outer spherical surface and a central passage, the central passage being sized and configured to receive the tapered central portion of the locking cap therein. Rotation of the nut may cause the bone fixation coupling element to move from a first position wherein the bridge member is able to angulate with respect to the locking cap via the bushing to a second position wherein when the bridge member is fixedly secured with respect to the locking cap.

In yet another exemplary embodiment of the transconnector, the transconnector may include a bridge member having a first end and a second end and first and second bone fixation coupling elements. Each of the bone fixation coupling elements may include at least one of a protrusion or recess formed thereon for engaging one of a protrusion or recess formed on an outer surface of the body portion of the bone fixation element. Each of the bone fixation coupling elements may also include a hole for receiving one of the first and second ends of the bridge member. The first and second ends of the bridge member may each include a locking element located thereon, the locking element including an unlocked position and a locked position. In the unlocked position, the bone fixation coupling elements are moveable with respect to the bridge member while in the locked position the bone fixation coupling elements are fixed with respect to the bridge member. The locking elements may include a locking sleeve and a collar, the locking sleeves being slidably disposed on the bridge member, the collar being slidably disposed on the locking sleeve, wherein movement of the collar with respect to the locking sleeve causes the locking element to move from the unlocked position to the locked position.

BRIEF DESCRIPTION OF THE DRAWINGS

The system is explained in even greater detail in the following exemplary drawings. The drawings are merely exemplary to illustrate the structure of preferred devices and features described herein may be used singularly or in combination with other features, and features shown in one embodiment may be readily applied to other embodiments. The claims should not be limited to the embodiments shown.

FIG. 17a is a partial perspective view of an alternate embodiment of a transconnector;

FIG. 17b is a perspective view of an exemplary bone fixation coupling element used in conjunction with the transconnector of FIG. 17a;

FIG. 17c is a side view of an exemplary embodiment of a set screw used in conjunction with the transconnector of FIG. 17a;

FIG. 17d is a perspective view of an exemplary embodiment of a housing used in conjunction with the transconnector of FIG. 17a;

FIG. 17e is a perspective view of an exemplary embodiment of a slider used in conjunction with the transconnector of FIG. 17a;

FIG. 17f is a cross-sectional view of the bone fixation coupling element used in connection with the transconnector of FIG. 17a, the bone fixation coupling element being in an opened position;

FIG. 17g is a cross-sectional view of the bone fixation coupling element used in connection with the transconnector of FIG. 17a, the bone fixation coupling element being in a closed position;

FIG. 18a is a partial perspective view of another exemplary embodiment of a transconnector;

FIG. 18b is a side view of the transconnector shown in FIG. 18a;

FIG. 19b is a cross-sectional view of the transconnector shown in FIG. 19a;

FIG. 20a is a cross-sectional view of another exemplary embodiment of a bone fixation coupling element, the bone fixation coupling element being in an opened position;

FIG. 20b is a cross-sectional view of the bone fixation coupling element shown in FIG. 20a, the bone fixation coupling element being in a closed position;

FIG. 21a is a perspective view of another exemplary embodiment of a bone fixation coupling element;

FIG. 21b is a side view of the bone fixation coupling element shown in FIG. 21a;

FIG. 22a is a perspective view of another exemplary embodiment of a bone fixation coupling element;

FIG. 22b is a cross-sectional view of the bone fixation coupling element shown in FIG. 22a;

FIG. 23 is a perspective view of another exemplary embodiment of a bone fixation coupling element;

FIG. 24 is a perspective view of another exemplary embodiment of a bone fixation coupling element.

DETAILED DESCRIPTION

Figure 1:
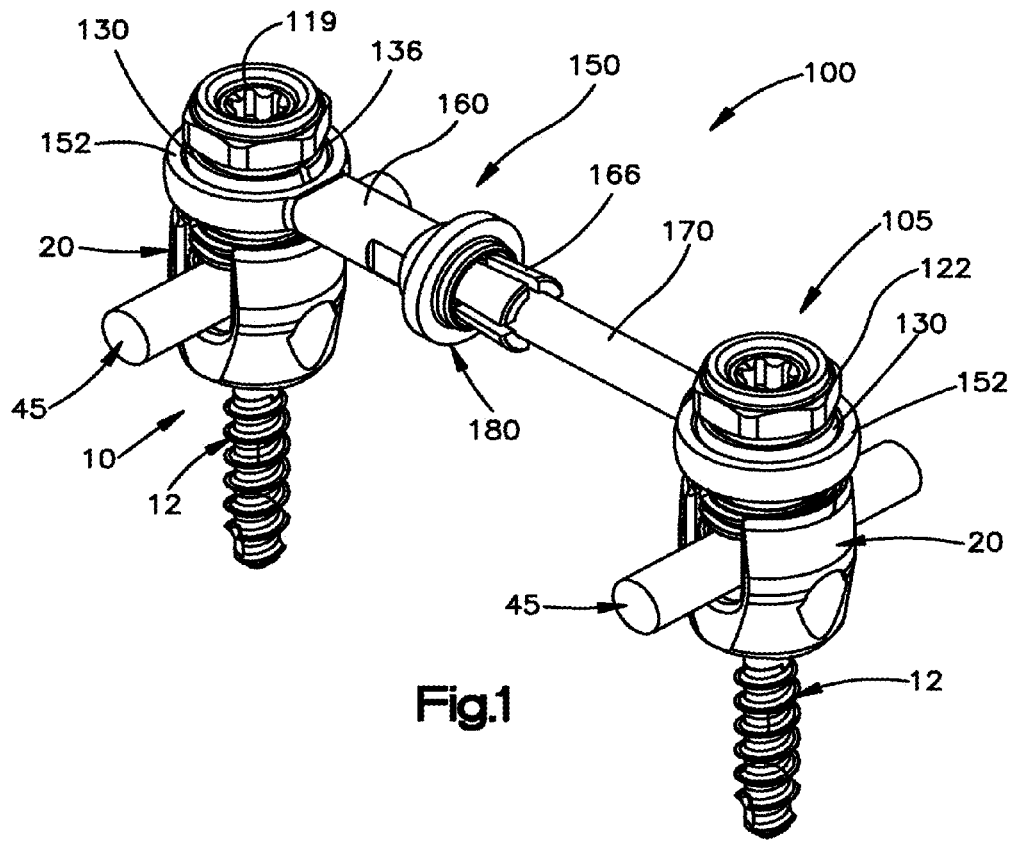
FIG. 1 is a perspective view of an exemplary embodiment of a transconnector.

Certain exemplary embodiments will now be described with reference to the drawings, wherein like reference numerals are used to refer to like elements throughout. In general, such embodiments relate to a cross-brace or transconnector (collectively referred to herein as a transconnector), by way of non-limiting example, a transconnector for use in interconnecting a pair of longitudinal spinal rods in a posterior spinal fixation procedure. The invention may have other applications and uses and should not be limited to the structure or use described and illustrated. As will be described in greater detail below, the transconnector preferably receives and/or engages the bone fixation element as opposed to the longitudinal spinal rod. By providing a transconnector that directly receives and/or engages the bone fixation element, the transconnector (i) may be generally easier to implant, (ii) may provide for a more robust and rigid fixation system as compared to known transconnectors and (iii) may minimize lateral profile.

In use, the transconnector preferably is configured to provide multiple degrees of freedom to permit the transconnector to accommodate varying spinal rod alignments. For example, the transconnector preferably may be configured to angulate and translate with respect to the bone fixation elements, thus permitting the transconnector to accommodate, for example, converging and/or diverging longitudinal spinal rods, non-coplanar longitudinal spinal rods, and longitudinal spinal rods that have varying rod separation distances.

Moreover, while the transconnector will be described as and may generally be used in the spine (for example, in the lumbar, thoracic or cervical regions), those skilled in the art will appreciate that the transconnector may be used for fixation of other parts of the body such as, for example, joints, long bones or bones in the hand, face, feet, etc. In addition, the transconnector may be used for external fixation of the body such as, for example, where rods are joined outside of the patient's body to, for example, the patient's vertebra, long bones, etc.

The transconnector may be constructed from any biocompatible material including, but not limited to, stainless steel, titanium, titanium alloys, polymers, memory shaped alloys, etc.

It should also be understood that the longitudinal spinal rod may include, but not be limited to, a solid rod, a non-solid rod, a flexible or dynamic rod, etc. Alternatively, the longitudinal spinal rod may not be a rod at all and may be in the shape of, for example, a plate. It should be understood that the transconnector is not limited in its use to any particular type of longitudinal spinal rod.

Figure 16:
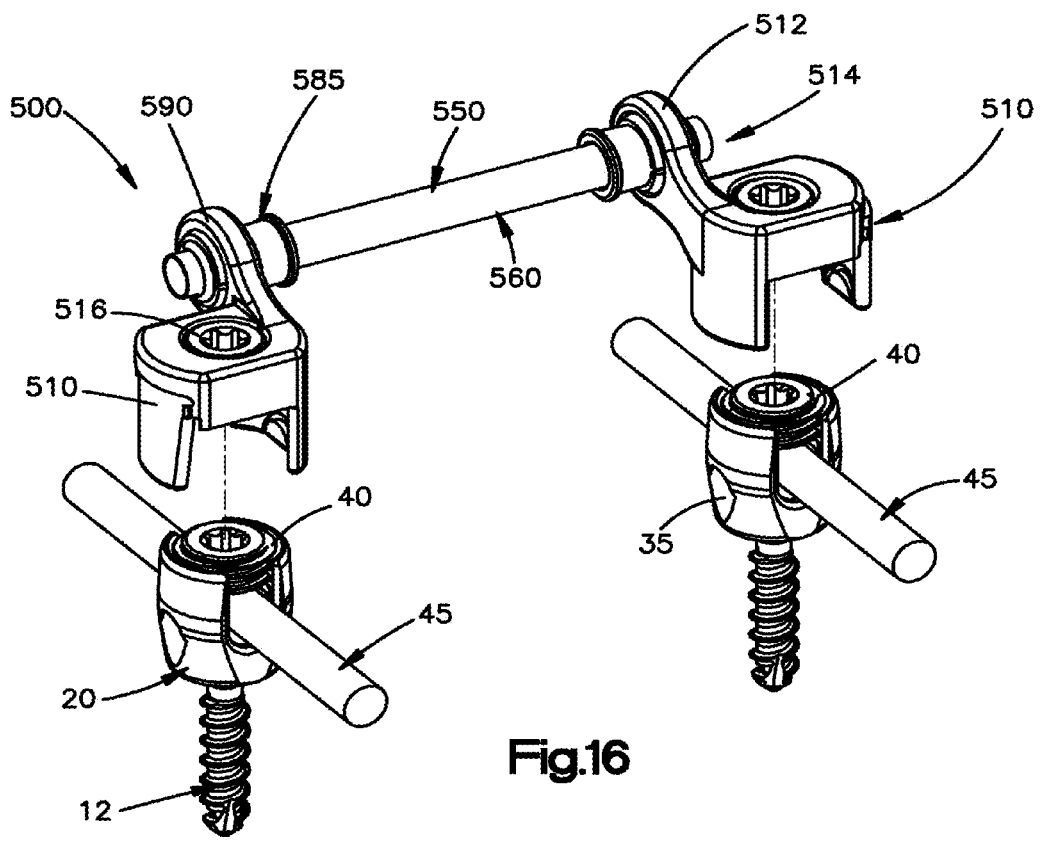
FIG. 16 is another perspective view of the transconnector shown in FIG. 15.

As will be described in greater detail below, the transconnector may be used in conjunction with bone fixation elements. As generally understood by one of ordinary skill in the art, it should be understood that bone fixation element is used generally and may include, but are not limited to, poly-axial or mono-axial pedicle screws, hooks (both mono-axial and poly-axial) including pedicle hooks, transverse process hooks, sublaminar hook, or other fasteners, clamps or implants. As generally shown in the FIGS., the bone fixation element 10 may include a bone anchor 12 (shown as a bone screw) having an enlarged head portion (not shown), a body portion 20 (shown as a top loading body portion) having a rod-receiving channel 25 (shown as a top loading V-shaped rod-receiving channel) defined by a pair of spaced apart arms 28,30. As generally known, the bone fixation elements 10 may include an insert assembly 32 (as shown, for example, in FIGS. 20a and 20b), the insert assembly 32 may be slidably disposed within the body portion 20. The insert assembly 32 may be a one piece insert member. Alternatively, the insert assembly 32 may be formed of two or more pieces. The bone fixation elements 10 also generally include a closure cap 40, as best shown in FIG. 16. In use, the enlarged end portion of the bone anchor 12 may be separate from and be disposed within the lower end of the body portion 20 so that the bone anchor 12 can poly-axial rotate with respect to the body portion 20. Alternatively, the bone anchor 12 may be formed integral with the body portion 20 to form a monolithic structure which is sometimes referred to as a mono-axial bone fixation element.

Once the spinal rod 45 is inserted into the rod-receiving channel 25, the surgeon can secure the position of the spinal rod 45 with respect to the body portion 20 and the position of the bone anchor 12 with respect to the body portion 20 by, for example, rotating the closure cap 40. Rotation of the closure cap 40 may cause the closure cap 40 to exert a downward force onto the spinal rod 45, which is received within the rod-receiving channel 25, which, in turn, causes the spinal rod 45 to exert a downward force onto the insert assembly 32 with may cause the insert assembly 32 to compress around the enlarged head portion of the bone anchor 12 thereby securing the position of the bone anchor 12 with respect to the body portion 20. In addition, rotation of the closure cap 40 may cause the spinal rod 45 to be sandwiched in-between the closure cap 40 and the insert assembly 32 thereby securing the position of the spinal rod 45 with respect to the body portion 20. It should be understood however that the transconnector is not limited in its use to any particular type of bone fixation element 10, and other styles, for example side loading, and other types, for example, no insert assembly, no insert member, no closure cap, etc. may be used.

Figure 2:
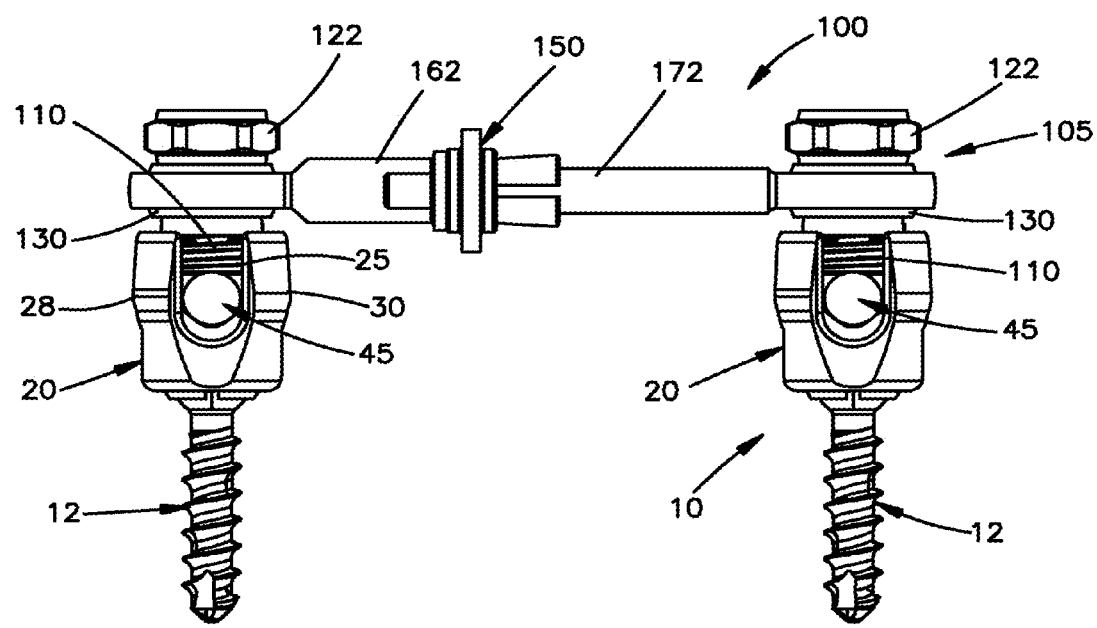
FIG. 2 is a side view of the transconnector shown in FIG. 1.
Figure 3:
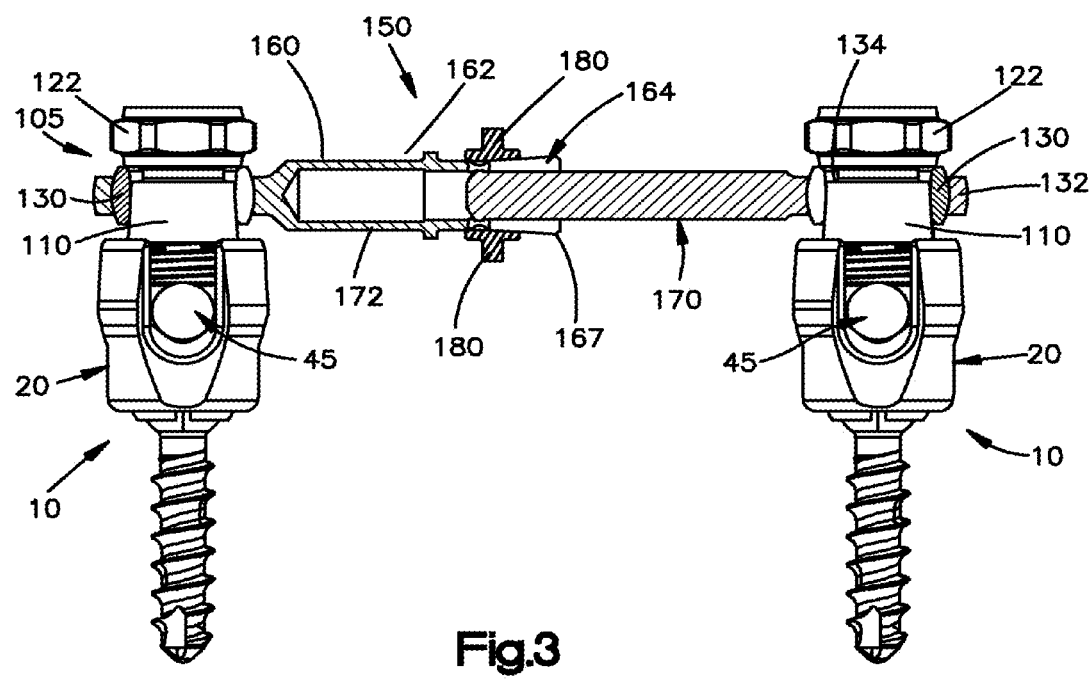
FIG. 3 is a cross-sectional view of the transconnector shown in FIG. 1.

As shown in FIGS. 1-4, the transconnector 100 may include a bone fixation coupling element 105 and a bridge member 150. The bone fixation coupling element 105 may include a locking cap 110, a bushing 130 and a nut 122. The bushing 130 is generally sized and configured to interconnect the locking cap 110 and bridge member 150 while facilitating movement of the bridge member 150 with respect to the locking cap 110 until the transconnector 100 is locked into position. As best shown in FIG. 3, the bushing 130 may include an outer surface 132 and a central passage 134, the central passage 134 being sized and configured for receiving the locking cap 110 therein, preferably the tapered central portion 118 of the locking cap 110, as will be described in greater detail below. The outer surface 132 of the bushing 130 may include an arcuate surface so that, in use, the bushing 130 enables and/or facilitates movement, preferably poly-axial movement, of the bridge member 150 with respect to the locking cap 110, and hence movement, preferably poly-axial movement, of the bridge member 150 with respect to the bone fixation element 10 attached thereto. By providing a poly-axial connection via the bushing 130, the need to bend the bridge member 150 in order to engage the locking cap 110 is substantially or completely eliminated. This in return substantially eliminates any pre-loading that may occur on the bone fixation element as a result of incorrect bending of the bridge member 150, which in turn could result in construct failure. In addition, providing a poly-axial connection substantially eliminates overall operating time and the necessity for trial and error by reducing the criticality of pre-selecting the correct bridge member 150. The bushing 130 may also include a slot 136 (as best shown in FIG. 1) formed therein. As will be appreciated by those of ordinary skill in the art, the slot 136 enables the bushing 130 to expand as it is moved over the tapered central portion 118 of the locking cap 110.

Figure 4:
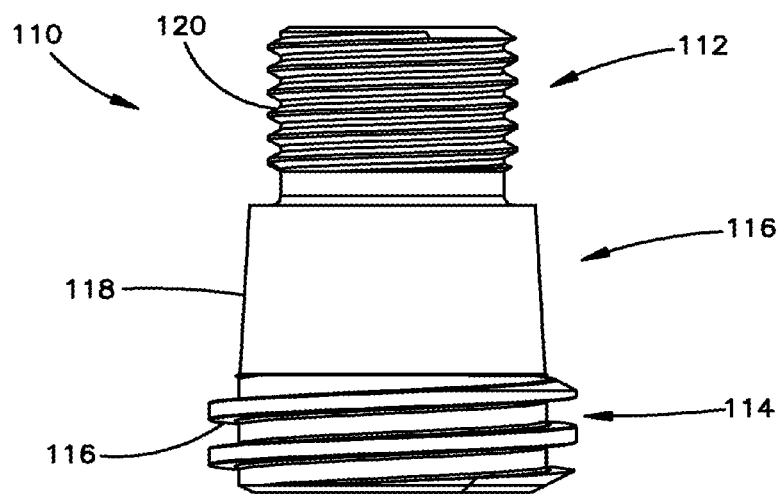
FIG. 4 is a side view of a locking cap used in conjunction with the transconnector of FIG. 1.

As best shown in FIG. 4, the locking cap 110 may include a proximal end 112, a distal end 114, and a central portion 116 located therebetween. The central portion 116 is preferably sized and configured to receive the bushing 130. The central portion 116 may include a tapered surface 118. The distal end 114 preferably includes a plurality of external threads 116 for engaging the internal threads formed on the bone fixation element 10. Alternatively, the distal end 114 may include internal threads for engaging external threads formed on the bone fixation element 10 or any other connection means including but not limited to snap-fit, partial cam lock, etc. In this manner, the locking cap 110 preferably directly engages the body portion 20 of the bone fixation element 10. In essence, in this embodiment, the locking cap 110 preferably replaces and/or acts as the closure cap 40 generally used in connection with bone fixation elements 10. The locking cap 110 also preferably includes a drive recess 119 for engaging a surgical instrument.

As shown, the proximal end 112 of the locking cap 110 may also include a plurality of external threads 120 for engaging an internally threaded nut 122. Alternatively, the proximal end 112 may include a plurality of internal threads for engaging an externally threaded nut or cap. Rotation of the threaded nut 122 causes the poly-axial connection of the bridge member 150 to the locking cap 110 via the bushing 130 to become fixed. That is, rotation of the threaded nut 122 causes the nut 122 to contact the top surface of the bushing 130, which in turn causes the bushing 130 to move downwards with respect to the locking cap 110. Downwards movement of the bushing 130 along the tapered central portion 118 of the locking cap 110 causes the bushing 130 to expand, which in turn causes the bushing 130 to become wedged in between the locking cap 110 and the bridge member 150, which in turn causes the position of the bridge member 150 to become fixed with respect to the locking cap 110, and hence with respect to the bone fixation element 10 and longitudinal spinal rod 45 affixed thereto.

In use, preferably the locking cap 110 and bushing 130 are sized and configured so that the bridge member 150 does not contact the body portion 20 of the bone fixation element 10. For example, the tapered central portion 118 of the locking cap 110 and the central passage 134 of the bushing 130 may be configured so that the bridge member 150 does not contact the body portion 20 of the bone fixation element 10. Alternatively, the locking cap 110 may include a ledge or a stop member, preferably a circumferential ledge, that prevents the bridge member 150 from contacting the body portion 20 of the bone fixation element 10 (as will be described in greater detail below).

During installation, a surgeon engages the nut 122 with a surgical instrument (e.g. a drive tool) that is sized and configured to simultaneously engage the drive recess 119 formed in the locking cap 110 and engages the nut 122 so that rotation of the surgical instrument causes the locking cap 110 to remain stationary with respect to the bone fixation element 10 while causing the nut 122 to rotate with respect to the locking cap 110. In this manner, rotation of the threaded nut 122 causes the nut 122 to contact the top surface of the bushing 130 thereby fixing the position of the bridge member 150 with respect to the locking cap 110, and hence with respect to the bone fixation element 10 and longitudinal spinal rod 45 affixed thereto, as previously described. By preventing the locking cap 110 from further rotating with respect to the bone fixation element 10, the possibility of over-tightening the locking cap 110, which may in turn cause splaying of the bone fixation element 10 resulting in the entire construct including the bone fixation element 10 to be replaced, is substantially prevented. Moreover, by preventing the locking cap 110 from further rotating with respect to the bone fixation element 10 and by preventing the bridge member 150 from contacting the body portion 20 of the bone fixation element 10, loading of the bone fixation element 10 is substantially reduced and/or eliminated, thus further reducing the likelihood of construct failure.

The bridge member 150 preferably includes at least one hole 152 formed on either end thereof for receiving the locking cap 110 and bushing 130. The bridge member 130 may also include a first member 160 and a second member 170 wherein the first and second members 160, 170 are moveable with respect to one another so that the length of the transconnector 100 can be adjusted to correspond with the distance between the bone fixation coupling elements 105 and hence the longitudinal spinal rods 45. By providing an adjustable length bridge member 150, the transconnector 100 is able to allow for varied medial to lateral adjustment. Alternatively, the bridge member 150 may be in the form of a single, nonadjustable fixed length member. Several fixed length bridge members 150 may be provided in a kit.

As shown in FIGS. 1-3, the first member 160 may be in the form of an outer telescoping rod 162 while the second member 170 may be in the form of an inner telescoping rod 172, wherein the inner telescoping member 172 is telescopically received within the outer telescoping rod 162. The outer telescoping rod 162 may be formed as a hollow cylinder having an internal bore 164 formed therein. The bore 164 being sized and configured to slidably receive the inner telescoping rod 172 so that the inner telescoping rod 172 can rotate about and translate along the longitudinal axis of the transconnector 100. The first and second members 160, 170 may also be formed as lateral side by side members that slide relative to one another to provide an adjustable length bridge member. Other arrangements of first and second members are also envisioned to construct an adjustable bridge member.

The bridge member 150 may also include a mechanism for fixing the position of the first and second members 160, 170 (e.g. the inner and outer telescopic rods 162, 172) with respect to one another. The mechanism may be any mechanism including but not limited to, for example, a screw, bolt, ratchet, etc. As shown, preferably the bridge member 150 may include a ring 180 disposed about the outer telescoping rod 162, the ring 180 being slidably disposed about the outer telescoping rod 162 from a first position to a second position wherein in the first position (as best shown in FIG. 3) the inner telescoping rod 172 is free to move with respect to the outer telescoping rod 162 but when the ring 180 is moved to the second position (as best shown in FIG. 2) the inner telescoping rod 172 is fixed with respect to the outer telescoping rod 172. Preferably, the outer telescoping rod 162 is sized and configured to be crush-locked or compressed by the ring 180 as the ring 180 is moved to the second position. As shown, the outer telescoping rod 162 may be configured with a plurality of slots 166 extending from an end thereof, at least a portion of the rod 162 adjacent the slots 166 preferably incorporates a thickened region and/or one or more projections 167 so that the slots 166 facilitate the crush locking of the outer telescoping rod 162 as the ring 180 is moved to the second position. That is, movement of the ring 180 from the first position to the second position causes the slots 166 formed in the outer telescoping rod 162 to compress resulting in the thickened region and/or projections 167 formed on the telescoping rod 162 to contact and secure the relative position of the inner telescoping rod 172.

Figure 5:
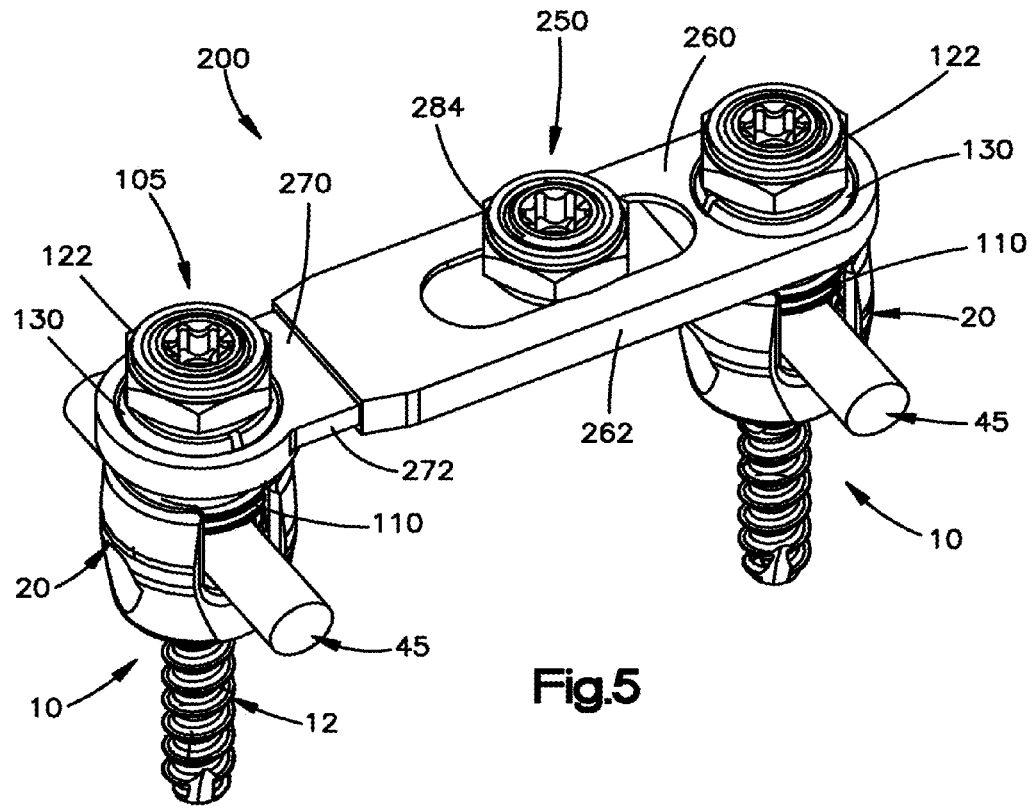
FIG. 5 is a perspective view of an alternate exemplary embodiment of a transconnector.
Figure 6:
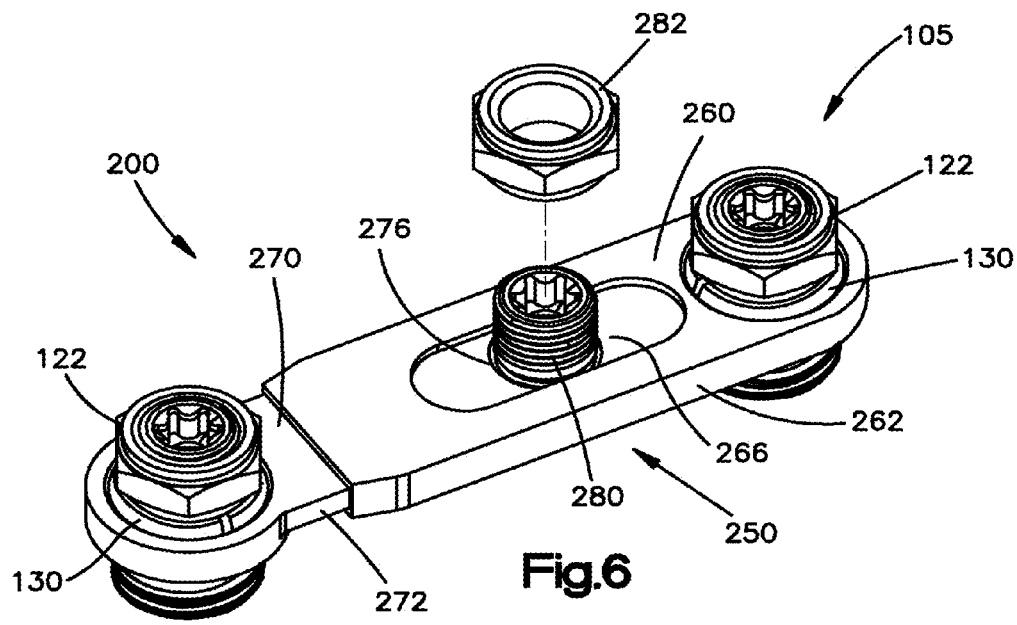
FIG. 6 is a partial perspective view of the transconnector shown in FIG. 5.
Figure 7:
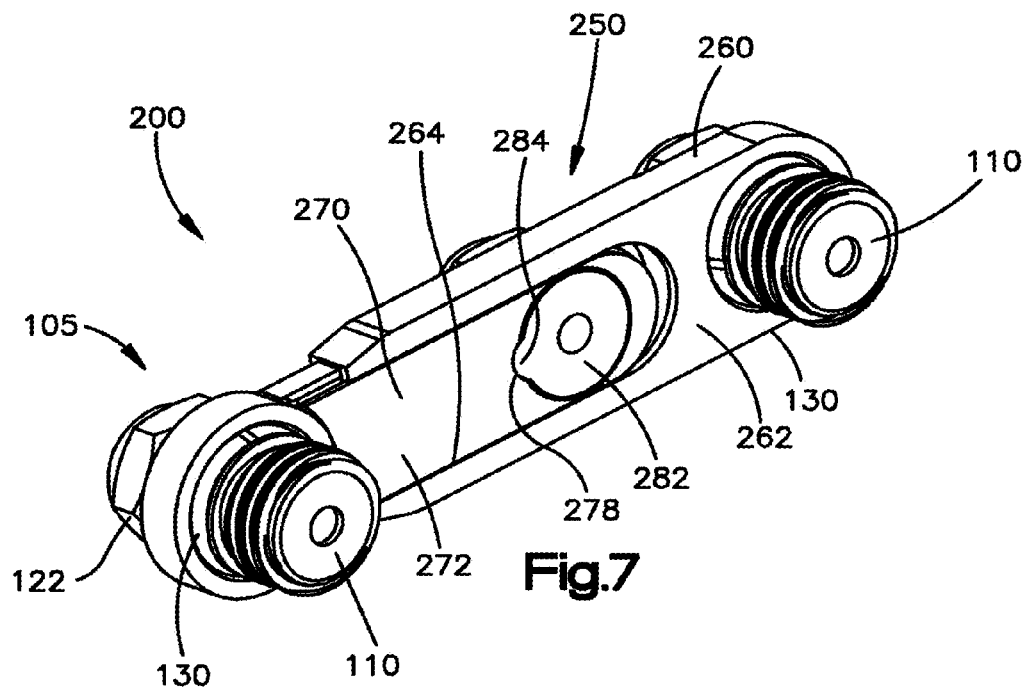
FIG. 7 is a bottom view of the transconnector shown in FIG. 5.

An alternate embodiment of a transconnector 200 is shown in FIGS. 5-7. In this embodiment, the first and second members 260, 270 of the bridge member 250 may be in the form of plate members 262, 272 wherein the second plate member 272 is slidable with respect to, and preferably receivable within, the first plate member 262 so that the second plate member 272 can translate with respect to the first plate member 262 along the longitudinal axis of the transconnector 200 to adjust the relative length of the transconnector 200. As best shown in FIG. 7, the first plate member 262 may include a tongue 264 for slidably receiving the second plate member 272.

The bridge member 250 may include a threaded fastener 280 and nut 282 for fixing the position of the second plate member 272 with respect to the first plate member 262. Although, as previously described, it should be noted that incorporation of other means for fixing the position of the first and second plate members 262, 272 with respect to one another is contemplated. More preferably, the first plate member 262 includes an elongated slot 266 while the second plate member 272 includes a hole 276 formed therein. The hole 276 being sized and configured to receive the threaded fastener 280. The hole 276 and fastener 280 are preferably sized and configured with a recess 278 and protruding lobe 284, respectively, to prevent the fastener 280 from spinning as the nut 282 is being rotated (as best shown in FIG. 7). In use, rotation of the nut 282 secures the relative positions of the first and second plate members 262, 272.

Since the bone fixation coupling element shown in FIGS. 5-7 is identical to the bone fixation coupling element 105 shown and discussed above in connection with FIGS. 1-4, discussion of the bone fixation coupling element is omitted.

Figure 8:
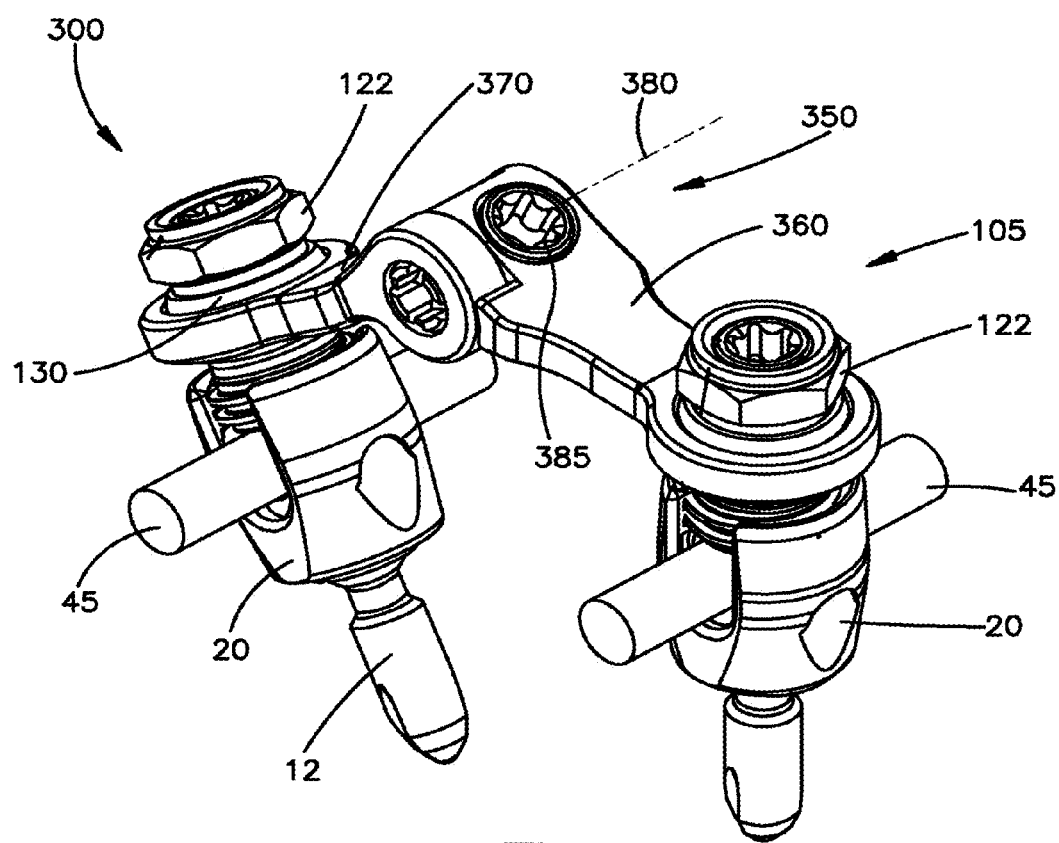
FIG. 8 is a perspective view of an alternate exemplary embodiment of a transconnector.
Figure 9:
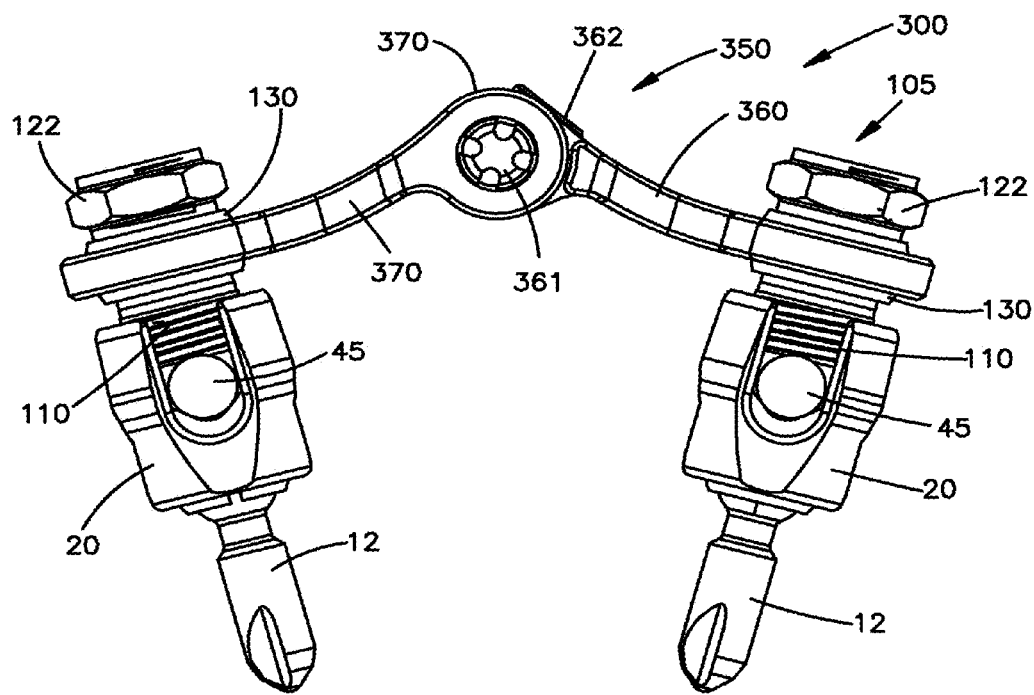
FIG. 9 is a side view of the transconnector shown in FIG. 8.
Figure 10:
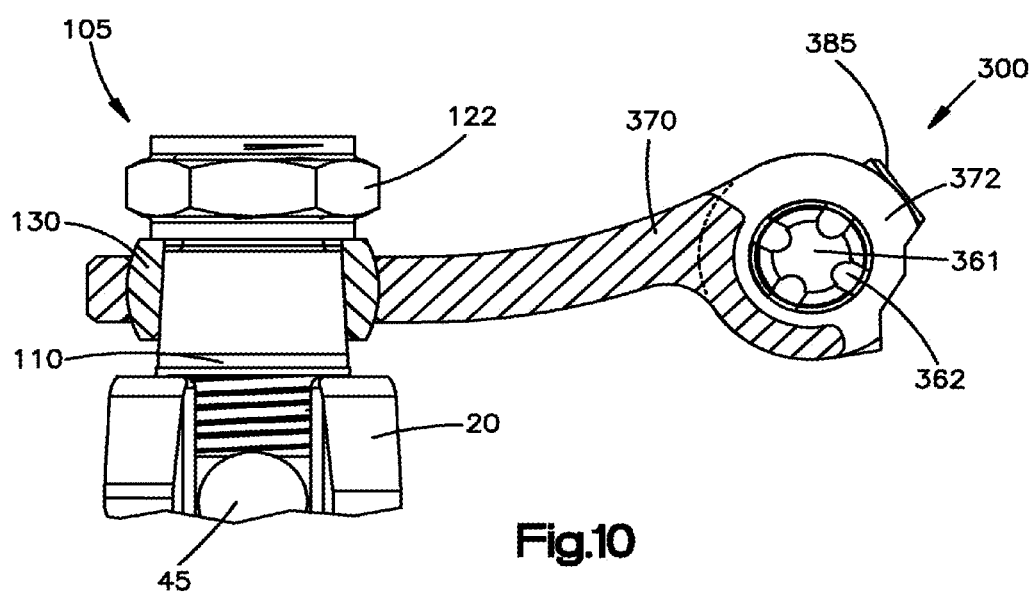
FIG. 10 is a partial cross-sectional view of the transconnector shown in FIG. 8.
Figure 11:
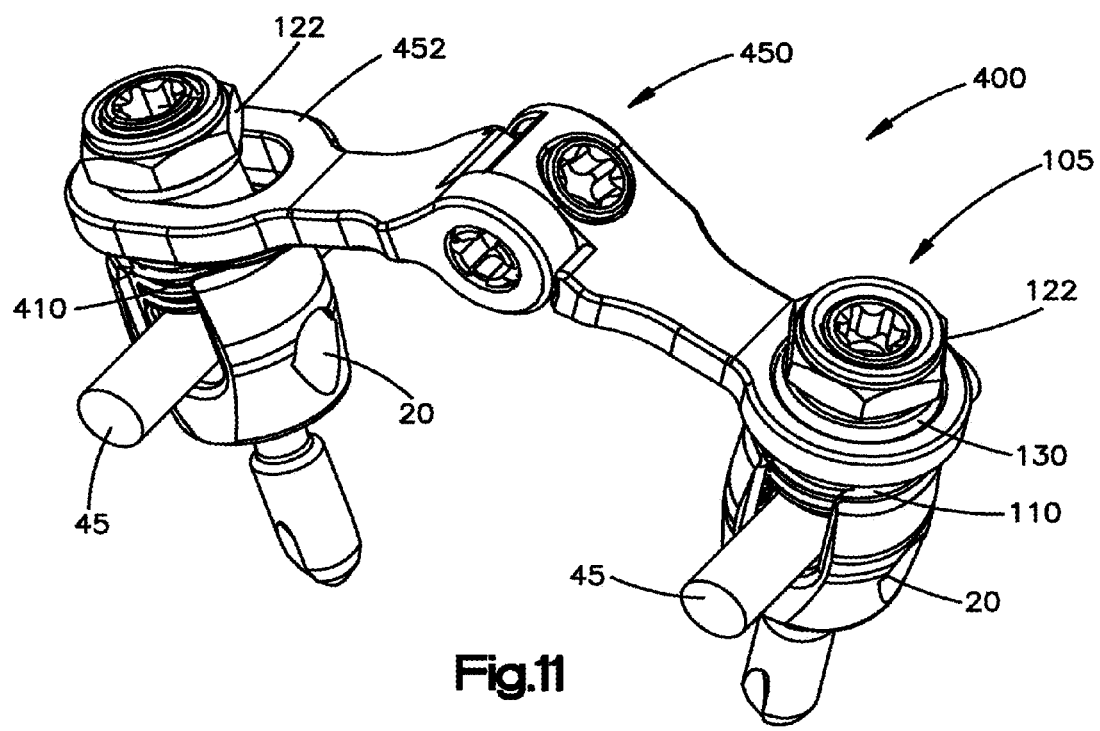
FIG. 11 is a perspective view of an alternate exemplary embodiment of a transconnector.
Figure 12:
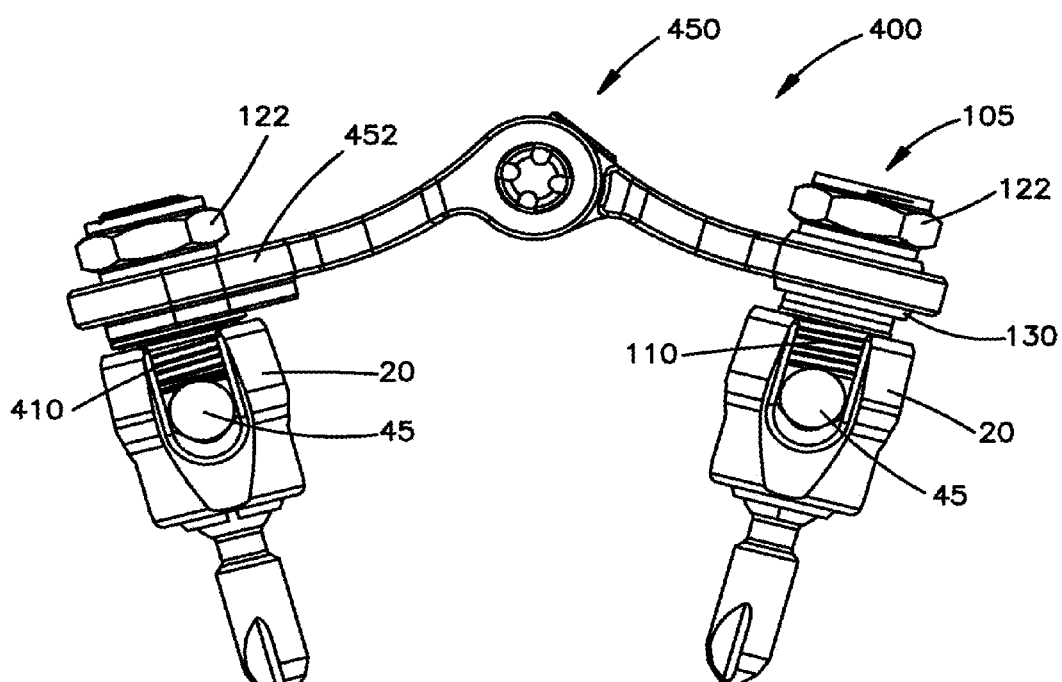
FIG. 12 is a side view of the transconnector shown in FIG. 11.
Figure 13:
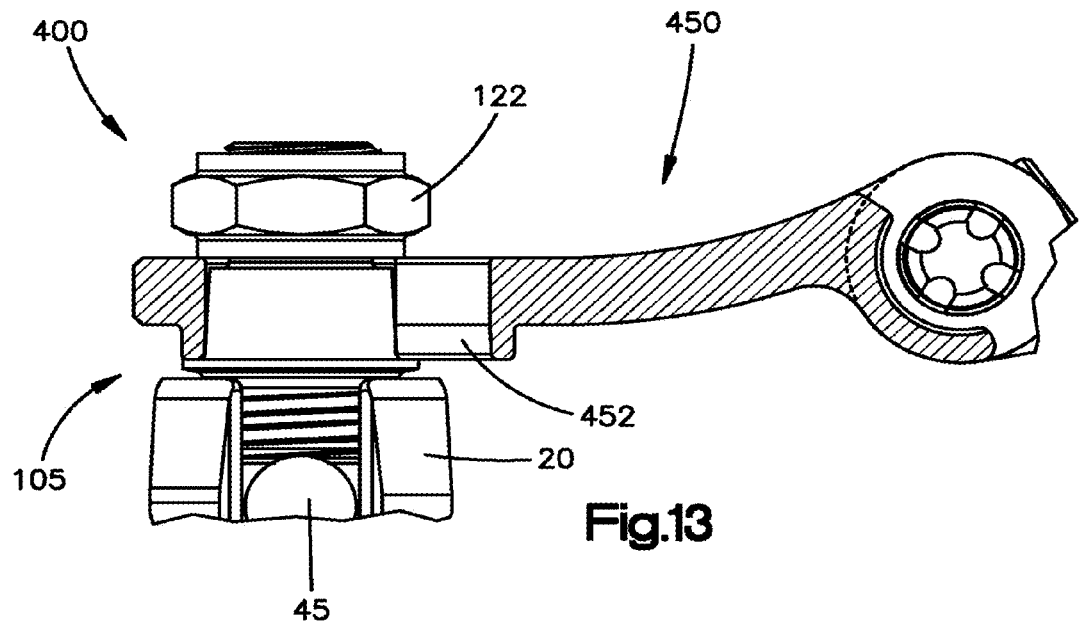
FIG. 13 is a partial cross-sectional view of the transconnector shown in FIG. 11.
Figure 14:
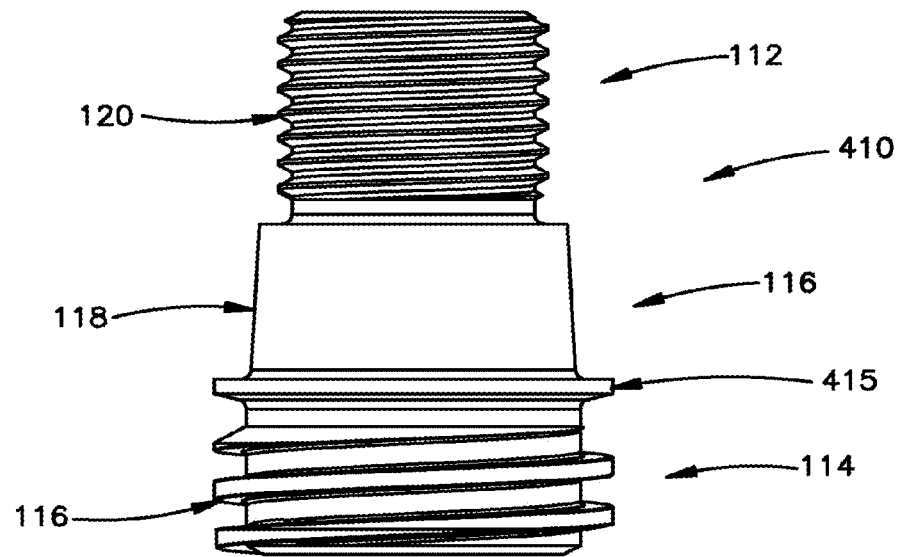
FIG. 14 is a side view of a locking cap used in conjunction with the transconnector of FIG. 11.

An alternate embodiment of a transconnector 300 is shown in FIGS. 8-10. In this embodiment, the bridge member 350 may be in the form of first and second members 360, 370 wherein the first member 360 is pivotally coupled or hinged to the second member 370. As shown, the first member 360 is preferably pivotally coupled or hinged to the second member 370 via a pivot axis 380 that may be substantially transverse to the longitudinal axis of the transconnector 300. That is, pivotal adjustment of the first and second members 360, 370 may cause the bridge member 350 to bend in the anatomical axial plane. In this manner, pivotable adjustment of the first member 360 with respect to the second member 370 will alter the length of the transconnector 300. Pivotal adjustment of the first member 360 with respect to the second member 370 may cause the bridge member 350 to move posteriorly thus shortening the overall length of the transconnector.

As shown, the second member 370 preferably includes a hole 372 formed therein, the hole 372 being sized and configured to receive a projection 361 extending from the first member 360, the projection 361 preferably includes a plurality of tabs 362. The bridge member 350 may further include a threaded fastener or set screw 385. The fastener 385 preferably being engageable with the first member 360 such that rotation of the fastener 385 causes the projection 361, more preferably the plurality of tabs 362, to expand thereby causing the position of the first member 360 to be fixed with respect to the second member 370.

Since the bone fixation coupling element shown in FIGS. 8-10 is identical to the bone fixation coupling element 105 shown and discussed above in connection with FIGS. 1-4, discussion of the bone fixation coupling element is omitted.

An alternate embodiment of a transconnector 400 is shown in FIGS. 11-14. In this embodiment, the bridge member 450 is substantially identical to the bridge member 350 discussed above in connection with FIGS. 8-10 except that one or both ends (shown as one end only) of the bridge member 450 may include an elongated slot 452 for receiving the locking cap 410 and to provide for additional medial-lateral adjustment of the transconnector. As will be appreciated by one of ordinary skill in the art, by providing an elongated slot 452, the transconnector 400 may be provided with additionally flexibility to engage the locking caps 110, 410. As shown, preferably, where an elongated slot 452 is incorporated, the bushing 130 maybe omitted. However, it should be understood that a bushing 130 can be used in conjunction with the elongated slot 452. Moreover, preferably where the bushing 130 is omitted, the locking cap 410 includes a circumference ledge or stop member 415 to prevent the bridge member 450 from contacting the bone fixation element 10 for reasons described above.

It should be noted that while it has only been described and shown as if transconnector 400 includes an elongated slot 452, any of the transconnectors described herein may be modified to include an elongated slot.

Since the other components of the bone fixation coupling element, including the bushing and nut shown in FIGS. 11-14 are identical to the bushing 130 and nut 122 discussed above in connection with FIGS. 1-4, discussion of these components is omitted.

In use, the bridge member may be provided pre-assembled. Moreover, the bridge member may be provided pre-assembled with the bushing attached thereto. Although, the bridge member may be provided in a pre-assembled form, the first and second members of the bridge member may be translationally and/or rotationally adjustable relative to one another. That is, for example, the first and second members of the bridge member may still be free to move (e.g., translate, rotate, etc.) with respect to one another.

After the bone fixation elements 10 have been implanted along the patient's vertebra in their desired orientation and location on either side of the patient's vertebral midline and after the longitudinal spinal rods 45 have been seated within the rod-receiving channels 25 of the bone fixation element 10, the locking cap may be used in lieu of the standard closure cap 40 to secure the longitudinal spinal rods 45 in the rod-receiving channels 25 of the bone fixation elements 10. Next, the bridge members may be installed between the pair of longitudinal spinal rods 45 by placing and/or securing the bridge member onto the locking caps. Preferably, as previously stated, the bushing and/or locking cap are sized and configured to prevent the bridge member from directly contacting the body portion 20 of the bone fixation element 10. The position, orientation, and/or length of the bridge member may then be adjusted until its desired position is achieved. Once achieved, the nut 122 may be tightened to fixedly secure the position of the bridge member with respect to the bone fixation element 10. In addition, movement of the ring 180, rotation of the nut 282, rotation of the screw 385, etc. may be performed in order to secure the relative position of the first and second members of the bridge member with respect to one another. Alternatively, movement of the ring 180, rotation of the nut 282, rotation of the screw 385, etc. may be performed prior to rotation of nut 122.

Figure 15:
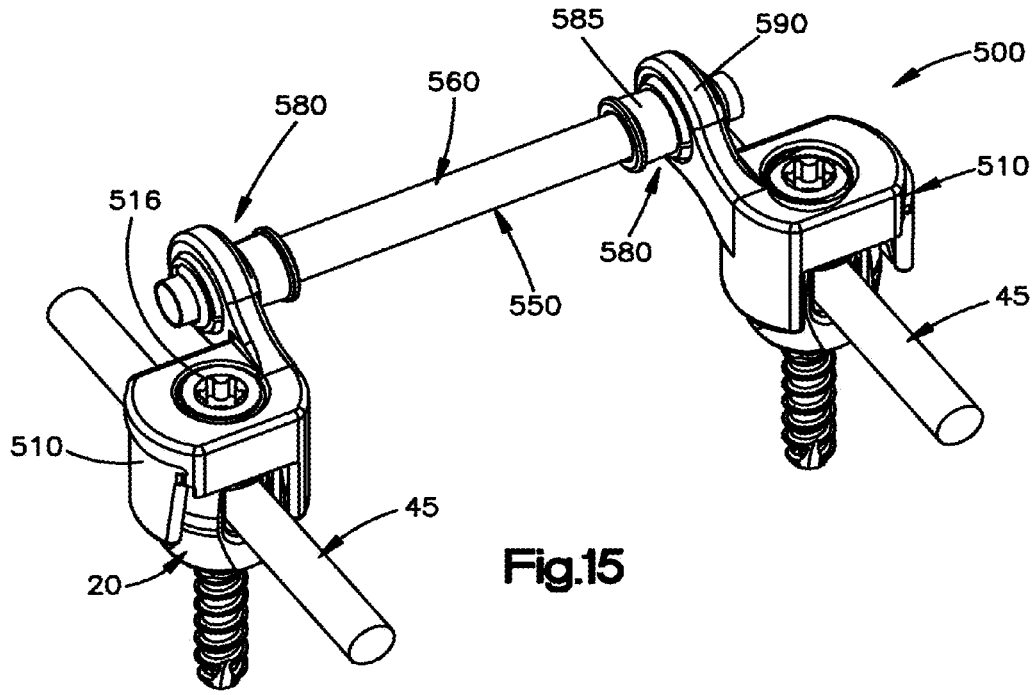
FIG. 15 is a perspective view of an alternate exemplary embodiment of a transconnector.

With reference to FIGS. 15 and 16, yet another exemplary embodiment of a transconnector 500 will be described. The transconnector 500 may include a pair of bone fixation coupling elements 510 and a bridge member 550.

As described in U.S. patent application Ser. No. 10/684,351 entitled Linking Transconnector for Coupling Spinal Rods, the entire contents of which are incorporated herein by reference, the bridge member 550 may be in the form of a lateral rod 560 having a locking element 580 located on and/or affixed to either end of the lateral rod 560. As shown, the lateral rod 560 may have a cylindrical cross-section area and a length sufficient to extend between adjacent bone fixation coupling elements 510. As will be appreciated by those skilled in the art, however, the lateral rod 560 may take on other suitable shape including but not limited to rectangular, square, plate-like, etc.

The locking element 580 may be sized and configured to provide for the secured fixation of the lateral rod 560 with respect to the bone fixation coupling element 510, and hence with respect to the bone fixation element 10 and longitudinal spinal rod 45 seated therein, once the desired position of the lateral rod 560 has been achieved. That is, the locking element 580 may be configured to move from a first position to a second position. In the first position, the locking element 580 may permit rotation and/or translational adjustment of the bone fixation coupling elements 510 with respect to the lateral rod 560. In the second position, the locking element 580 may fix, both rotationally and translationally, the position of the lateral rod 560 with respect to the associated bone fixation coupling elements 510, thus fixing the relative position of the lateral rod 560 with respect to the longitudinal spinal rods 45. The locking element 580 may be configured to the second position through the application of a force to the locking element 580.

The locking element 580 may include a locking sleeve 585 and a collar 590. Alternatively, however, the locking element 580 may take on other embodiments, for example, the locking element 580 may be in the form of a single, monolithic component which may directly interconnect the bone fixation coupling elements 510 and the lateral rod 560.

The locking sleeve 585 may be sized and configured to be slidably positionable along the length of the lateral rod 560 thereby permitting the transconnector 500 to accommodate varying medial lateral distances between longitudinal spinal rods 45. As shown, the locking sleeve 585 may be in the form of a generally cylindrical member having a through bore extending therethrough. The through bore preferably is sized and shaped for receiving the lateral rod 560, while the outer surface of the locking sleeve 585 is sized and shaped to receive the through bore of the collar 590, as will be described in greater detail below. More preferably, the through bore of the locking sleeve 580 has a size permitting receipt of the lateral rod 560 in a sliding manner thus enabling the transconnector 500 to accommodate varying distances between longitudinal spinal rods 45 by sliding the locking elements 580 along the length of the lateral rod 560.

The locking sleeve 585 preferably has a tapered outer surface extending from an end thereof, such that the diameter of the outer surface of the locking sleeve 585 adjacent the one end is greater than the diameter of the outer surface of the locking sleeve 585 adjacent the other end. The locking sleeve 585 also preferably includes a through wall slit which extends from one end to the other. The slit preferably allows the locking sleeve 585 to expand to facilitate installation of the locking sleeve 585 onto the lateral rod 560. The slit also preferably allows the locking sleeve 585 to contract around the lateral rod 560, such as when a force is applied to the locking sleeve 585 to fix the location of the lateral rod 560 with respect to the locking element 580, as will be described in greater detail below.

As previously stated, the locking element 580 may also include a collar 590, the collar 590 having any appropriate shape for positioning between the locking sleeve 585 and the bone fixation coupling element 510. The collar 590 may be sized and configured to be positioned between the locking sleeve 585 and the bone fixation coupling element 510 thereby permitting the lateral rod 560 to be universally adjustable with respect to the bone fixation coupling elements 510, and thus enabling the lateral rod 560 to be universally adjustable with respect to the longitudinal spinal rods 45. That is, the collar 590 preferably includes a convex outer surface for engaging an inner concave surface formed on the bone fixation coupling element 510, thereby facilitating universal adjustment of the lateral rod 560 with respect to the bone fixation coupling element 510. This universal adjustment permits the transconnector 500 to accommodate varying spinal rod alignments including, for example, converging or diverging spinal rods and non-coplanar spinal rods 45.

The collar 590 may also include a through bore extending therethrough, the through bore being sized and shaped for receiving the locking sleeve 585 and the lateral rod 560 therein. Preferably, the collar 590 has an overall length shorter than the overall length of the locking sleeve 585 so that the collar 590 is sized and dimensioned to be slidably positionable between the ends of the locking sleeve 585 so that the collar 590 may be adjustably positionable along the length of the locking sleeve 585. The collar 590 may also include a through wall slit that extends from a first end to a second end thereof, the slit permitting easier installation of the collar 590 onto the locking sleeve 585. That is, similar to the slit formed on the locking sleeve 585, the slit formed on the collar 590 allows the collar to be expanded to allow for easier installation.

In addition to facilitating installation of the individual transconnector components during assembly, the slits formed in the locking sleeve 585 and collar 590 allow the two pieces to be axially and rotationally locked together. That is, the outer surface of the locking sleeve 585 preferably has a diameter near the first end which is sized to be smaller than the diameter of the unexpanded through bore of the collar 590, while the outer surface of the locking sleeve 585 has a diameter near the second end which is sized to be larger than the diameter of the unexpanded through bore of the collar 590. Thus, when the collar 590 is positioned adjacent the first end of the locking sleeve 585, the locking sleeve 585 and collar 590 may move freely with respect to each other. However, when the collar 590 is positioned adjacent the second end of the locking sleeve 585, the larger diameter of the locking sleeve 585 interferes with the inner surface of the collar 590, causing a frictional lock between the locking sleeve 585 and the collar 590. This force may cause the locking sleeve 585 to compress against the outer surface of the lateral rod 560 while simultaneously causing the collar 590 to expand to engage the bone fixation coupling element 510, thereby locking the relative positions of the lateral rod 560 and the locking element 580 both rotationally and translationally, with respect to one another. That is, this locking action preferably causes a slight compression of the locking sleeve 585 and a slight expansion of the collar 590 preferably facilitating frictional locking of the locking sleeve 585 to the lateral rod 560 and frictionally locking of the collar 590 to the bone fixation coupling element 510.

As previously stated, the transconnector 500 may also include a pair of bone fixation coupling elements 510. The bone fixation coupling elements 510 are preferably sized and configured to, one the one hand, engage the bone fixation elements, preferably the body portion 20 of the bone fixation elements 10 and, on the other hand, engage the bridge member 550 via the locking elements 580.

As shown, the bridge member 550 may include a lateral rod engaging portion 512 having an opening 514 sized and configured to receive the bridge member 550 (e.g. lateral rod 560) and the locking element 580. The opening 514 may have an inner concave surface for adjustably receiving the outer convex surface of the locking element 580, preferably the collar 590, thus providing a spherical adjustment assembly. Alternatively, the opening 514 may have an inner convex surface for adjustably receiving the outer concave surface of the collar 590. This spherical adjustment configuration permits the lateral rod 560 to be universally adjustable with respect to each bone fixation coupling element 510, and thus to the longitudinal spinal rods 45, thereby permitting the transconnector 500 to easily accommodate a wide variety of spinal rod alignments.

Although the lateral rod engaging portion 512 is described herein and shown as having an annular or circular shape, the lateral rod engaging portion 512 may take on any suitable shape for receiving the bridge member 550 (e.g. lateral rod 560) and the locking element 580 including, but not limited to, oval, elliptical, square, rectangular, etc. Preferably, the engaging surfaces of the lateral rod engaging portion 512, the lateral rod 560, and the locking element 580 all have a substantially similar shape. It should be noted that the bone fixation coupling elements 510 may be connected to the bridge member 550 by any other known means including, but not limited to, a mechanical connection such as, for example, a screw.

As previously stated, the bone fixation coupling elements 510 also preferably include a mechanism for directly engaging the bone fixation elements 10, more preferably the body portion 20 of the bone fixation elements 10. The bone fixation coupling elements 510 may be engaged to the body portion 20 of the bone fixation element 10 by any means including but not limited to a snap-fit connection, a press-fit connection, a tongue and groove type connection, a mechanical connection such as, for example, a threaded screw, bolt, etc. As best shown in FIGS. 15 and 16, the bone fixation coupling elements 510 are preferably sized and configured to receive the body portion 20 of the bone fixation element 10 so that, after the bone fixation element 10 has been implanted into the patient's body and the longitudinal spinal rod 45 has been seated and secured within the rod-receiving channel 25 of the bone fixation element 10, the bone fixation coupling elements 510 can be placed over and pressed down onto the body portion 20 of the bone fixation element 10. Preferably, the bone fixation coupling element 510 may be sized and configured to be press-fitted or snap-fitted onto the body portion 20 of the bone fixation element 10. More preferably, the body portion 20 of the bone fixation element 10 may include one or more recesses 35 formed on the outer surface of the body portion 20, the recesses 35 being sized and configured to engage a protrusion 635 (as best shown in FIGS. 17*d* and 17*e*) formed on the inner surface of the bone fixation coupling elements 510 such that as the bone fixation coupling elements 510 are placed over the body portion 20 of the bone fixation elements 10 and pressed downwards, the protrusion 635 formed on the bone fixation coupling elements 510 may engage the recess 35 formed in the body portion 20 of the bone fixation element 10.

In addition and/or alternatively, the bone fixation coupling elements 510 may include a fastener 516 that is sized and configured to threadably engage the bone fixation element 10. As shown, the fastener 516 may be sized and configured to threadably engage internal threads formed on the closure cap 40. In this manner, the bone fixation elements 10 may be secured to the patient's vertebrae in their desired locations. The longitudinal spinal rods 45 may be seated and secured within the rod-receiving channels 25 of the bone fixation elements 10 via a closure cap 40 as generally known by one of ordinary skill in the art. Next, the transconnectors 500 may be connected to the bone fixation elements 10 in their desired positions and/or as required. Alternatively, the closure cap 40 may be removed from the body portion 20 and the fastener 516 may be sized and configured to directly engage the internal threads formed in the body portion 20 of the bone fixation element 10.

In use, the transconnector 500 may be provided pre-assembled, such that the bone fixation coupling elements 510 and the locking elements 580 are provisionally attached to each end of the bridge member 550 (e.g. lateral rod 560). Although, the transconnector 500 may be provided in a pre-assembled form, the lateral rod 560 and bone fixation coupling elements 510 may be translationally and/or rotationally adjustable relative to one another. That is, the locking sleeve 585 may still be free to translate along the lateral rod 560 and the spherical adjustment assembly of the collar 590 and bone fixation coupling element 510 permits the bone fixation coupling element 510 to universally rotate with respect to the lateral rod 560.

Next, the pre-assembled transconnector 500 may be installed onto the bone fixation elements 10 between a pair of longitudinal spinal rods 45 by placing and pressing the bone fixation coupling elements 510 over the desired bone fixation elements 10. The bridge member 550 may then be adjusted, both rotationally and translationally, until its desired position is achieved. Once achieved, the bone fixation coupling elements 510 may be fixedly secured to the bone fixation elements 10. Thereafter, a tool may be used to engage the locking sleeve 585 and collar 590, and the two components 585, 590 may be moved with respect to one another using the tool. Movement of the collar 590 with respect to the locking sleeve 585 causes the locking sleeve 585 to slide within the collar 590, which, due to the increasing taper of the locking sleeve 585 causes interference between the outer surface of the locking sleeve 585 and the inner surface of the collar 590. This interference causes the locking sleeve 585 to compress and the collar 590 to expand, thereby fixing the position of the locking sleeve 585 to the lateral rod 560, the collar 590 to the bone fixation coupling element 510, and the locking sleeve 585 to the collar 590. All engagement between elements are frictional in nature, such that a reverse application of force between the collar 590 and the locking sleeve 585 may cause the components to disengage such that they are again adjustable with respect to each other.

In contrast to the one piece bone fixation coupling element 510 discussed above in connection with FIGS. 15 and 16, the bone fixation coupling elements may alternatively be in the form of a multi-piece bone fixation coupling element 610, as best shown in FIGS. 17a-17g. The multi-piece bone fixation coupling element 610 may include a housing 620 and a slider 630, wherein the slider 630 is sized and configured to be slidably received by the housing 620. Preferably, as shown, the housing 620 includes a recess 622 for slidably receiving a projection 632 formed on the slider 630 so that the slider 630 and housing 620 may be interconnected via a dovetail joint type connection. As shown, the housing 620 may also include a threaded hole 624 for receiving a set screw 625, the set screw 625 including a post 626 formed thereon for centering the transconnector in the drive recess 42 of the closure cap 40 of the bone fixation element 10. The slider 630 may also include a through hole 634 formed therein for permitting the post 626 to past therethrough. This preferably allows at least a portion of the set screw 625 to travel through the slider 630.

As best shown in FIGS. 17f and 17g, in use, the slider 630 may be slidably received within the housing 620 and the set screw 625 may be threaded against the threaded hole 624 formed in the housing 620. In the opened position, as best shown in FIG. 17f, the bone fixation coupling element 610 may be loosely placed on and/or over the body portion 20 of the bone fixation element 10 such that the protrusion 635 formed on the housing 620 may be engaged with the recess 35 formed on one side of the body portion 20 of the bone fixation element 10. However, in the open position, the protrusion 635 formed on the slider 630 may not be engaged with the recess 35 formed on the other side of the body portion 20. Alternatively, the protrusion 635 formed on the slider 630 may be engaged with the recess 35 formed on the body portion 20 while the protrusion 635 formed on the housing 620 may not be engaged with the recess 35 formed on the body portion 20. Alternatively, neither the protrusion 635 formed on the housing 620 and the slider 630 may be engaged with the recess 35 formed on the body portion 20. Rotation of the set screw 625 into the housing 620 causes the set screw 625, preferably the conical bottom surface of the set screw 625, to contact the slider 630, preferably the boundary of the through hole 634 formed in the slider 630. Thereafter, continued rotation of the set screw 625 causes the slider 630 to be drawn in with respect to the housing 620 and causes the slider 630 to move towards the body portion 20 of the bone fixation element 10. As best shown in FIG. 17g, when the set screw 625 is fully engaged with respect to the housing 620, the protrusion 635 formed on the slider 630 may engage the recess 35 formed on the other side of the body portion 20 of the bone fixation element 10 thereby securing the position of the bone fixation coupling member 610 with respect to the bone fixation element 10.

It should be noted that the housing 620 and slider 630 are preferably configured with a mechanism to prevent disassembly of the housing 620 and slider 630 with respect to one another. The mechanism may be any mechanism known in the art including, for example, deforming the housing 620 from the side through the dovetail recess while the slider 630 is located therein.

The bone fixation coupling elements may also directly engage the body portion 20 of the bone fixation elements 10 in other ways. For example, as shown in FIGS. 18a and 18b, the bone fixation coupling element 710 may be provided in such a fashion that all degrees of freedom are fixedly secured through the tightening of a single screw 725. That is, in this embodiment, preferably movement of the bridge member 750 with respect to the bone fixation coupling element 710 and movement of the longitudinal spinal rod 45 with respect to the bone fixation element 10 is fixedly secured by rotation of a single screw 725 with respect to the body portion 20.

As shown, the bridge member 750 may be formed as a solid bar 752 having a pair of eyelets 754 on either end thereof. The eyelets 754 being sized and configured to receive the bone fixation coupling element 710. It should be noted however that the bridge member 750 may be provided in different forms, for example, the bridge member 750 may be in the form of a plate, a rod, etc.

The bone fixation coupling element 710 may be in the form of a housing 720 wherein the housing 720 is sized and configured to receive the body portion 20 of the bone fixation element 10. The housing may be in the form of the one piece housing disclosed above in connection with FIGS. 15 and 16 or the two-piece housing 720 disclosed above in connection with FIGS. 17a-17g.

The bone fixation coupling element 710 may also include a circumferential recess 712 extending at least partially thereon, the circumferential recess 712 being sized and configured to receive one of the eyelets 754 formed on the bridge member 750. The eyelets 754 and the bone fixation coupling elements 710 preferably being sized and configured to permit the bone fixation coupling element 710 to translate with respect to the bridge member 750. In use, the bone fixation coupling element 710, which is connected to the bridge member 750, may be temporarily located on the body portion 20 of the bone fixation element 10 by aligning the protrusion 635 formed on the bone fixation coupling elements 710 with the recesses 35 formed on the body portion 20 of the bone fixation element 10. In this position, the bridge member 750 is preferably free to move in the medial-lateral direction as well as rotationally about the bone fixation element 10. Once the desired position of the bridge member 750 has been achieved, rotation of the set screw 725 preferably causes (i) the position of the bone fixation coupling element 710 to be secured with respect to the bone fixation element 10 by directly or indirectly applying a force to the longitudinal spinal rod which is seated within the rod-receiving channel and (ii) the position of the bone fixation coupling element 710 to be secured with respect to the bridge member 750 by radially expanding the housing 720 against the bridge member 550, preferably by radially expanding the housing 720 against the inner surface of the eyelet 754.

Figure 19B:
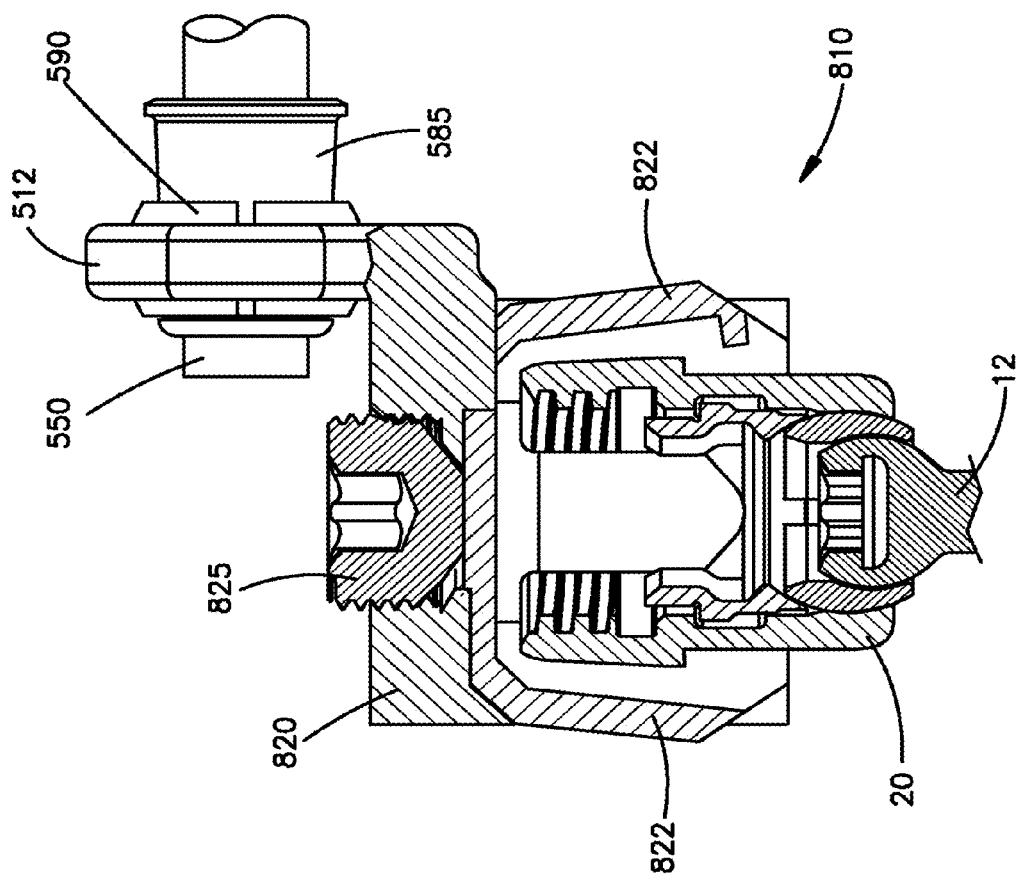
Figure 19A:
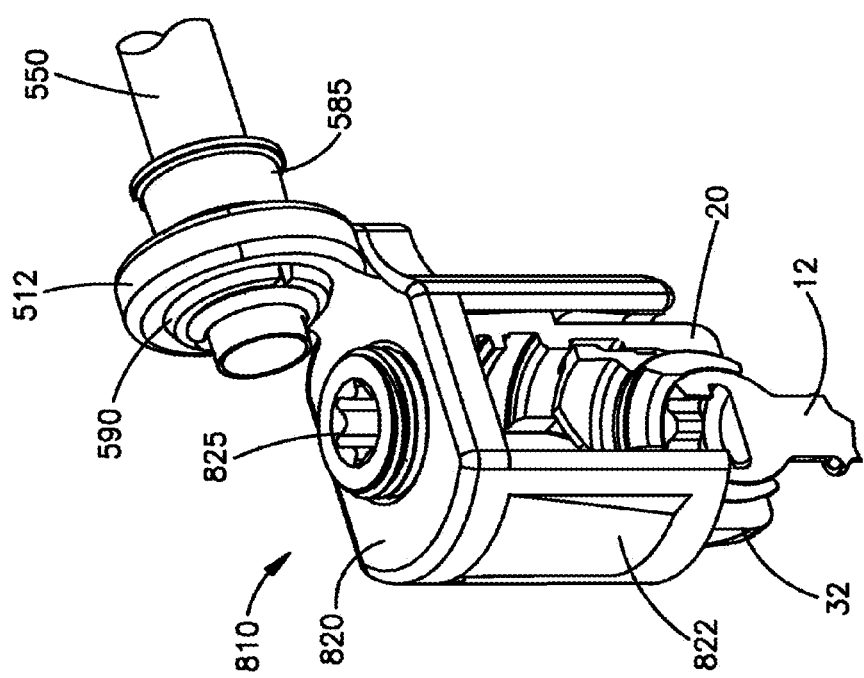
FIG. 19a is a partial perspective view of another exemplary embodiment of a transconnector.

In yet another embodiment, as best shown in FIGS. 19a and 19b, the bone fixation coupling element 810 may include a housing 820 that is sized and configured to receive the body portion 20 of the bone fixation element 10. The housing 820 may also include one or more beam elements 822, the beam elements 822 being sized and configured so that, upon rotation of the set screw 825, the set screw 825 causes the beam elements 822 to contact the body portion 20, preferably the recesses 35 formed in the body portion 20, of the bone fixation element 10. More specifically, rotation of the set screw 825 may cause the housing 820 to move upwards with respect to the body portion 20 of the bone fixation element 10 while simultaneously causing the beam elements 822 to move downwards and inwards into contact with the recesses 35 formed in the body portion 20 of the bone fixation element 10, thus securing the position of the bone fixation coupling element 810 with respect to the bone fixation element 10.

In yet another embodiment, as best shown in FIGS. 20a and 20b, the bone fixation coupling element 910 may include a housing 920, the housing 920 being sized and configured to receive the body portion 20 of the bone fixation element 10.

The housing 920 may also include a recess 922 for receiving one or more slide elements 930, wherein insertion of the slide elements 930 causes the housing 920 to engage the bone fixation element 10, preferably the protrusion 935 formed on the housing 920 to engage the recesses 35 formed on the body portion 20 of the bone fixation element 10. More specifically, as shown, in this embodiment, the set screw 825 of FIGS. 19a and 19b is replaced by one or more slide elements 930, wherein downwards movement of the slide element 930 causes the housing 920 to engage the body portion 20 of the bone fixation element 10.

In yet another embodiment, as best shown in FIGS. 21a and 21b, the bridge member 1050 may be formed with an integral bone fixation coupling element 1010. More particularly, as shown, the bridge member 1050 may include a ledge 1060 having a threaded bore 1062 for receiving a set screw 1025. The set screw 1025 being sized and configured to threadably engage the closure cap 40 of the bone fixation element 10. More preferably, as shown, the ledge 1060 formed on the bridge member 1050 and the closure cap 40 of the bone fixation element 10 are sized and configured with corresponding grind patterns 1075 (e.g. teeth, serrations, ridges, etc.). The grind pattern 1075 acts to provide additional fixation, both axially and rotationally, upon engagement of the set screw 1025.

In yet another embodiment, as best shown in FIGS. 22a and 22b, the bone fixation coupling element 1110 may include an intermediary component 1120 that is sized and configured for insertion into the rod-receiving channel 20 of the bone fixation element 10. The intermediary component 1120 being further sized and configured to contact the longitudinal spinal rod 45. The intermediary component 1120 further including a bore 1122 formed therein for receiving the closure cap 40 so that the closure cap 40 can be received within the rod receiving channel 25 of the bone fixation element 10 in engagement with the internal threads formed on the body portion 20 of the bone fixation element 10. Rotation of the closure cap 40 may cause the intermediary component 1120 to contact the longitudinal spinal rod 45 thereby fixing the position of the longitudinal spinal rod 45 with respect to the bone fixation element 10 and the position of the transconnector with respect to the bone fixation element 10.

In yet another embodiment, as best shown in FIG. 23, the bone fixation coupling element 1210 may include a housing 1220 that is sized and configured to receive the body portion 20 of the bone fixation element 10. The housing 1220 preferably being sized and configured to receive the body portion 20 of the bone fixation element 10 via an interference or press fit type connection. The bone fixation coupling element 1210 may also include a locking component 1230, the locking component 1230 being slidably moveable with respect to the housing 1220 from a first position to a second position, wherein in the second position the locking component 1230 further compresses the housing 1220 into engagement with the body portion 20 of the bone fixation element 10 in order to provide additional assurances and/or rigidity to prevent the bone fixation coupling element 1210 from becoming loose with respect to the bone fixation element 10.

In yet another embodiment, as best shown in FIG. 24, the bone fixation coupling element 1310 may include a housing 1320 that is sized and configured to receive the body portion 20 of the bone fixation element 10. The body portion 20 of the bone fixation element 10 preferably including a groove 1335 formed therein, the groove 1335 preferably extending from a top surface of the body portion 20. The groove 1335 being sized and configured to slidably receive the housing 1310. Preferably, the groove 1335 is sized and configured to slidably receive a tongue 1330 formed on the housing 1320. In this manner, the housing 1320 and body portion 20 of the bone fixation element 10 may be engaged via a key-type or tongue and groove type arrangement. The bone fixation coupling element 1310 may also include a set screw 1325 such that rotation and/or engagement of the set screw 1325 with the housing 1320 and/or bone fixation element 10 may provide additional assurances and/or rigidity to prevent the bone fixation coupling element 1310 from becoming loose with respect to the bone fixation element 10. Rotation of the set screw 1325 may cause the housing 1320 to move slightly upwards causing the protrusion formed on the housing 1320 to engage the recess 35 formed on the body portion 20 of the bone fixation element 10.

Figure 25:
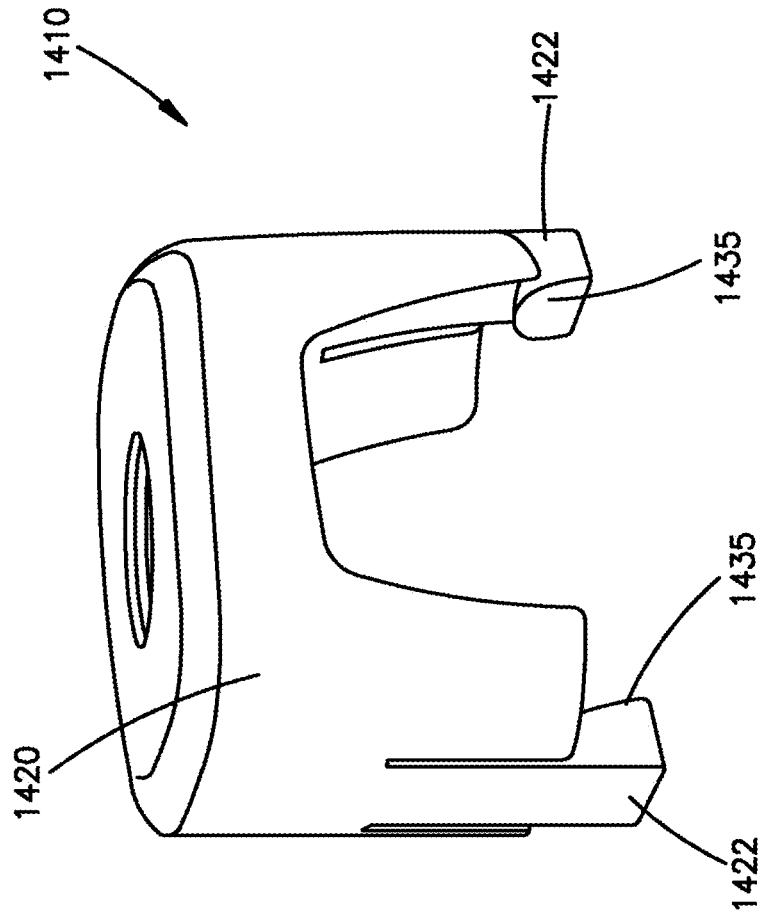
FIG. 25 is a perspective view of another exemplary embodiment of a bone fixation coupling element.

In yet another embodiment, as best shown in FIG. 25, the bone fixation coupling element 1410 may include a housing 1420 that is sized and configured to receive the body portion 20 of the bone fixation element 10. The housing 1420 preferably including a pair of fingers 1422 that are biased together so that the fingers 1422 can engage the body portion 20 of the bone fixation element 10 in a snap fit type arrangement. More preferably, the fingers 1422 each preferably include a protrusion 1435 formed thereon for engaging and/or snap fitting into recesses 35 formed in the body portion 20 of the bone fixation element 10. The bone fixation coupling element 1410 may further include a set screw (not shown) for threadably engaging the housing 1420 and/or bone fixation element 10 in order to further secure the bone fixation coupling element 1410, and hence the bridge member, to the bone fixation element 10.

While it has been generally described and shown as if the bone fixation coupling element includes one or more protrusions formed thereon for engaging one or more recesses formed on the body portion of the bone fixation element, it should be noted that the bone fixation coupling element may be configured with one or more recesses for engaging one or more protrusions formed on the bone fixation element.

Moreover, it should be noted, that although some embodiments of the bone fixation coupling elements have been described as being used in connection with bone fixation elements wherein the longitudinal spinal rod has already been fixedly secured within the rod-receiving channel of the bone fixation element via the closure cap and other embodiments have been described as being used in connection with bone fixation elements wherein the longitudinal spinal rod has not been fixedly secured within the rod-receiving channel of the bone fixation element via the closure cap, it is envisioned that the designs of the various bone fixation coupling elements can be modified and/or adapted such that the closure cap is no longer required for all embodiments, and vice versa.

As will be appreciated by those skilled in the art, any or all of the components described herein such as, for example, the bridge member, the bone fixation coupling elements, etc. may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same component may be provided in different shapes and/or sizes.

While the foregoing description and drawings represent the preferred embodiments of the present invention, it will be understood that various additions, modifications, combinations and/or substitutions may be made therein without departing from the spirit and scope of the invention as defined in the accompanying claims. For example, while numerous bridge members and/or bone fixation coupling elements have been described herein, it is envisioned that the different bridge members and bone fixation coupling elements can be mixed and matched such that every bridge member may be configured to be used in connection with each and every bone fixation coupling element. For example, the bridge members of FIGS. 1-14 may be used in connection with the bone fixation coupling elements disclosed in FIGS. 15-25. Similarly, the bridge members of FIGS. 15-25 may be used in connection with the bone fixation coupling element of FIGS. 1-14. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. For example, the transconnectors disclosed herein can be used to link and provide stability to both poly-axial and mono-axial screw pairs, or combinations thereof, in both medial-lateral and cranial-caudal constructs, as well as to link and provide stability to parallel rods constructs. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A transconnector for joining adjacent longitudinal spinal rods, the spinal rods being secured to a patient's vertebra via a plurality of bone fixation elements, each of the bone fixation elements including a body portion having a rod-receiving channel for receiving one of the longitudinal spinal rods, the transconnector comprising:
   a bridge member having a first end and a second end; and
   first and second bone fixation coupling elements,
      wherein the first and second bone fixation coupling elements are sized and configured to engage the first and second ends of the bridge member,
      wherein the first and second bone fixation coupling elements are each sized and configured to engage one of the bone fixation elements, each of the bone fixation coupling elements including a locking cap, a bushing and a nut, the bushing being sized and configured to interconnect the locking cap with the bridge member, the locking cap including a first set of threads for engaging the bone fixation element, a second set of threads for engaging the nut, and a non-threaded central portion located between the first set of threads and the second set of threads,
      wherein the second set of threads has an outer diameter that is less than the first set of threads,
      wherein the central portion is tapered and has an outer diameter less than the outer diameter of the first set of threads and greater than the outer diameter of the second set of threads.

2. The transconnector of claim 1, wherein the bridge member includes a second member moveably associated with a first member.

3. The transconnector of claim 2, wherein the first member has a form of an outer telescopic rod and the second member has a form of an inner telescopic rod, the outer telescopic rod having an internal bore for receiving the inner telescopic rod.

4. The transconnector of claim 3, wherein the bridge member further includes a ring disposed about the outer telescopic rod, the ring being slidably disposed about the outer telescopic rod from a first position to a second position wherein when the ring is in the first position, the inner telescopic rod is free to move with respect to the outer telescopic rod, and wherein when the ring is in the second position the inner telescopic rod is fixed with respect to the outer telescopic rod.

5. The transconnector of claim 4, wherein the outer telescopic rod includes a plurality of slots extending from an end thereof such that movement of the ring from the first position to the second position compresses at least a portion of the outer telescopic rod against the inner telescopic rod.

6. The transconnector of claim 2, wherein the first member is in the form of a first plate member and the second member is in the form of a second plate member, the second plate member being slidably receivable with respect to the first plate member, the first and second plate members being further sized and configured to receive a threaded fastener and a nut for securing a position of the second plate member with respect to the first plate member.

7. The transconnector of claim 2, wherein the first and second members are pivotally coupled to one another about a pivot axis substantially transverse to a longitudinal axis of the transconnector.

8. The transconnector of claim 1, wherein the central portion includes a taper.

9. The transconnector of claim 8, wherein the bushing includes an outer spherical surface and a central passage, the central passage being sized and configured to receive the taper of the central portion of the locking cap therein.

10. The transconnector of claim 8, wherein the taper of the central portion is sized and configured to prevent the bridge member from contacting the bone fixation element.

11. The transconnector of claim 1, wherein when the bone fixation coupling element is in a first position, the bridge member is able to angulate with respect to the locking cap via the bushing and wherein when the bone fixation coupling element is in a second position, the bridge member is fixedly secured with respect to the locking cap.

12. The transconnector of claim 11, wherein rotation of the nut causes the bone fixation coupling element to move from the first position to the second position.

13. The transconnector of claim 1, wherein the first set of threads threadably engage an internal threaded bore formed in the bone fixation element.

14. The transconnector of claim 1, wherein the second set of threads threadably engage an internal threaded bore formed in the nut.

15. The transconnector of claim 1, wherein the bridge member includes at least one hole formed on either end thereof for receiving the locking cap and the bushing.

16. A transconnector for joining adjacent longitudinal spinal rods, the spinal rods being secured to a patient's vertebra via a plurality of bone fixation elements, the bone fixation elements including a bone anchor and a body portion having a rod-receiving channel formed therein, the transconnector comprising:
   a bridge member having a first end and a second end; and
   first and second bone fixation coupling elements,
      wherein the first and second ends of the bridge member each includes at least one hole for receiving the first and second bone fixation coupling elements, respectively,
      wherein each of the bone fixation coupling elements includes a locking cap, a bushing and a nut, and wherein the locking cap includes a first set of threads for engaging the bone fixation element, a second set of threads for engaging the nut, and a non-threaded tapered central portion located between the first set of threads and the second set of threads, wherein the second set of threads has an outer diameter that is less than the first set of threads, wherein the central portion has an outer diameter less than the outer diameter of the first set of threads and greater than the outer diameter of the second set of threads, and wherein the bushing includes an outer spherical surface and a central passage, and wherein the central passage is sized and configured to receive the taper of the central portion of the locking cap therein.

17. The transconnector of claim 16, wherein rotation of the nut causes the bone fixation coupling element to move from a first position wherein the bridge member is able to angulate with respect to the locking cap via the bushing to a second position wherein when the bridge member is fixedly secured with respect to the locking cap.

18. The transconnector of claim 16, wherein the first set of threads threadably engage an internal threaded bore formed in the bone fixation element, and wherein the second set of threads threadably engage an internal threaded bore formed in the nut.

19. A transconnector for joining adjacent longitudinal spinal rods, the spinal rods being secured to a patient's vertebra via a plurality of bone fixation elements, the transconnector comprising:

a telescopically adjustable bridge member; and a pair of bone fixation coupling elements, wherein the telescopically adjustable bridge member is sized and configured to span a distance between the pair of bone fixation coupling elements and wherein each of the bone fixation coupling elements is sized and configured to engage the bridge member, the bone fixation coupling elements further including a locking cap for threadably engaging a plurality of threads formed on a body portion of the bone fixation element, wherein the locking cap includes a first set of threads for engaging the bone fixation element, a second set of threads for engaging a nut that is adapted to create a poly-axial connection of the telescopically adjusting bridge member to the locking cap, and a non-threaded central portion located between the first set of threads and the second set of threads, wherein the second set of threads has an outer diameter that is less than the first set of threads, wherein the central portion is tapered and has an outer diameter less than the outer diameter of the first set of threads and greater than the outer diameter of the second set of threads.

\* \* \* \* \*